United States Patent
Ryu et al.

(10) Patent No.: US 11,655,205 B2
(45) Date of Patent: May 23, 2023

(54) COMPOUND FOR ORGANIC OPTOELECTRONIC DEVICE AND ORGANIC OPTOELECTRONIC DEVICE AND DISPLAY DEVICE

(71) Applicant: SAMSUNG SDI CO., LTD., Yongin-si (KR)

(72) Inventors: Dong Wan Ryu, Suwon-si (KR); Jinhyun Lui, Suwon-si (KR); Hyunji Yoo, Suwon-si (KR); Youngkyoung Jo, Suwon-si (KR); Seungchul Lyu, Suwon-si (KR); Min Seok Seo, Suwon-si (KR); Ho Kuk Jung, Suwon-si (KR); Sung-Hyun Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 276 days.

(21) Appl. No.: 17/008,956

(22) Filed: Sep. 1, 2020

(65) Prior Publication Data
US 2021/0070689 A1 Mar. 11, 2021

(30) Foreign Application Priority Data
Sep. 11, 2019 (KR) .................. 10-2019-0113159

(51) Int. Cl.
*H01L 51/00* (2006.01)
*C07C 211/54* (2006.01)
*H01L 51/50* (2006.01)

(52) U.S. Cl.
CPC ........ *C07C 211/54* (2013.01); *H01L 51/0059* (2013.01); *H01L 51/5056* (2013.01)

(58) Field of Classification Search
CPC ............ C07C 211/54; H01L 51/0059; H01L 51/5056
See application file for complete search history.

(56) References Cited

U.S. PATENT DOCUMENTS

| 6,586,120 B2 * | 7/2003 | Tao ............... C09B 57/008 548/440 |
| 2002/0182439 A1 | 12/2002 | Tao et al. |
| 2007/0104778 A1 * | 5/2007 | Zeng ............... A61K 9/205 514/217 |
| 2016/0372666 A1 * | 12/2016 | Ryu ............... C07D 409/12 |
| 2021/0126213 A1 * | 4/2021 | Seo ............... C07D 209/86 |

FOREIGN PATENT DOCUMENTS

| CN | 103187537 A | 7/2013 |
| CN | 106164061 A | 11/2016 |
| CN | 110724062 A * | 1/2020 ........... C07C 211/54 |
| CN | 112250585 A | 1/2021 |
| JP | 07301928 A * | 11/1995 |
| JP | H07-301928 A | 11/1995 |
| JP | 2009-149850 A | 7/2009 |
| JP | 2011-006405 A | 1/2011 |
| JP | 5202759 B2 | 2/2013 |
| KR | 10-2012-0014913 A | 2/2012 |
| KR | 10-2012-0060611 A | 6/2012 |
| KR | 10-2013-0121597 A | 11/2013 |
| KR | 10-2015-0130221 A | 11/2015 |
| KR | 10-2016-0011522 A | 2/2016 |
| KR | 10-2017-0030450 A | 3/2017 |
| KR | 10-2017-0048159 A | 5/2017 |
| KR | 10-2017-0134132 A | 12/2017 |
| WO | WO 2010/137601 A1 | 12/2010 |
| WO | WO 2016-060332 A1 | 4/2016 |
| WO | WO-2016060332 A1 * | 4/2016 ............. C09K 11/06 |

OTHER PUBLICATIONS

CAS/CAPLUS Abstract and Indexed Compounds for W. Kang et al., CN 110724062 (Jan. 1, 2020) (Year: 2020).*
Chinese Office action dated Nov. 24, 2022.

* cited by examiner

*Primary Examiner* — Alexander R Pagano
(74) *Attorney, Agent, or Firm* — Lee IP Law, P.C.

(57) ABSTRACT

A compound for an organic optoelectronic device, an organic optoelectronic device, and a display device including the same, the compound being represented by Chemical Formula 1:

[Chemical Formula 1]

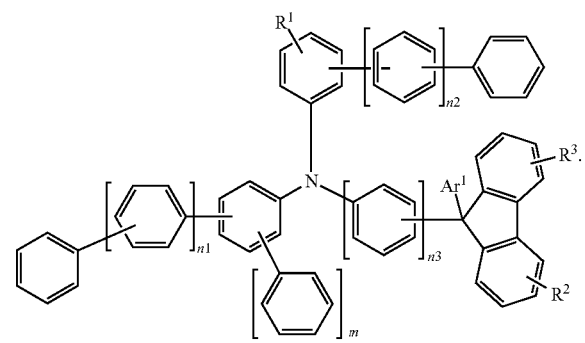

8 Claims, 1 Drawing Sheet

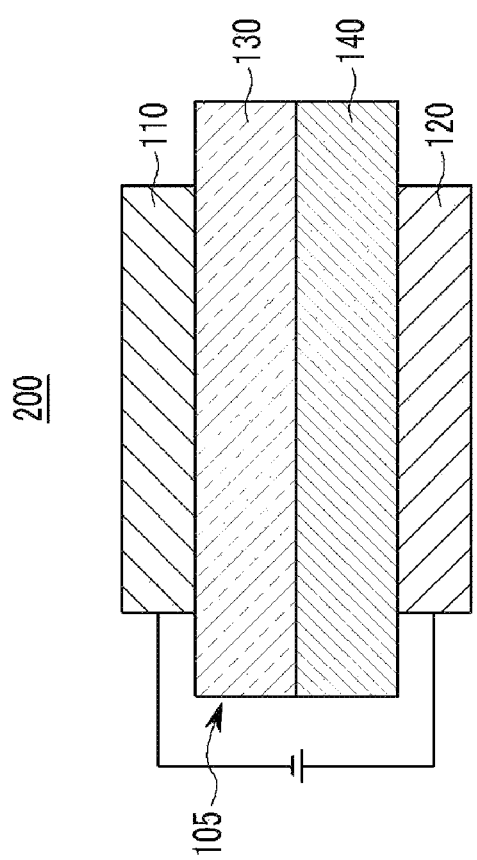

COMPOUND FOR ORGANIC OPTOELECTRONIC DEVICE AND ORGANIC OPTOELECTRONIC DEVICE AND DISPLAY DEVICE

CROSS-REFERENCE TO RELATED APPLICATION

Korean Patent Application No. 10-2019-0113159, filed on Sep. 11, 2019, in the Korean Intellectual Property Office, and entitled: "Compound for Organic Optoelectronic Device and Organic Optoelectronic Device and Display Device," is incorporated by reference herein in its entirety.

BACKGROUND

1. Field

Embodiments relate to a compound for an organic optoelectronic device, an organic optoelectronic device, and a display device.

2. Description of the Related Art

An organic optoelectronic device (e.g., an organic optoelectronic diode) is a device that converts electrical energy into photoenergy, and vice versa. An organic optoelectronic device may be classified as follows in accordance with its driving principles. One is a photoelectric device where excitons generated by photoenergy are separated into electrons and holes and the electrons and holes are transferred to different electrodes respectively and electrical energy is generated, and the other is a light emitting device to generate photoenergy from electrical energy by supplying a voltage or a current to electrodes.

Examples of the organic optoelectronic device include an organic photoelectric device, an organic light emitting diode, an organic solar cell, and an organic photo conductor drum.

Among them, the organic light emitting diode (OLED) has recently drawn attention due to an increase in demand for flat panel displays.

SUMMARY

The embodiments may be realized by providing a compound for an organic optoelectronic device, the compound being represented by Chemical Formula 1:

[Chemical Formula 1]

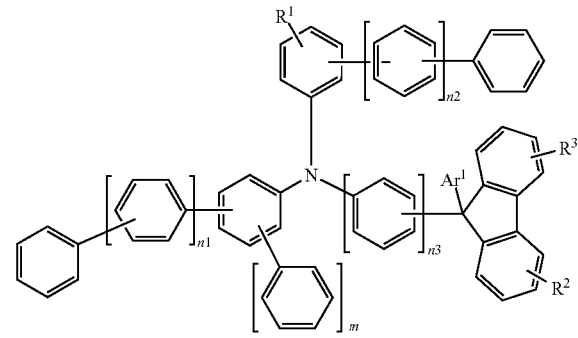

wherein, in Chemical Formula 1, $Ar^1$ is a substituted or unsubstituted C6 to C30 aryl group, $R^1$ to $R^3$ are independently hydrogen, deuterium, a cyano group, a halogen, a substituted or unsubstituted C1 to C10 alkyl group, or a phenyl group, n1 and m are independently 0 or 1, n1+m=1, n2 is an integer of 0 to 2, and n3 is 1 or 2.

Chemical Formula 1 may be represented by Chemical Formula 1A or 1B,

[Chemical Formula 1A]

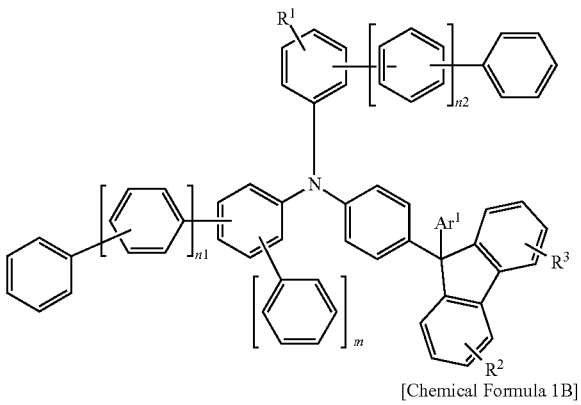

[Chemical Formula 1B]

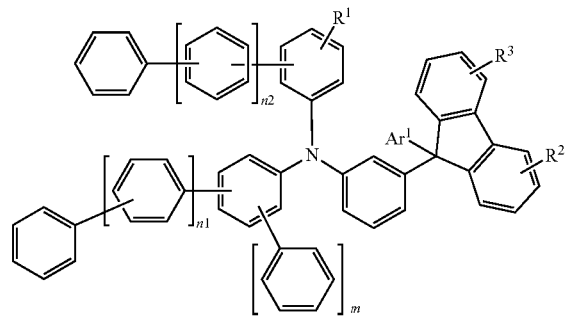

in Chemical Formula 1A and Chemical Formula 1B, $Ar^1$ is a substituted or unsubstituted C6 to C30 aryl group, $R^1$ to $R^3$ are independently hydrogen, deuterium, a cyano group, a halogen, a substituted or unsubstituted C1 to C10 alkyl group, or a phenyl group, n1 and m are independently 0 or 1, n1+m=1, and n2 is an integer of 0 to 2.

Chemical Formula 1 may be represented by Chemical Formula 1C, Chemical Formula 1D, or Chemical Formula 1E,

[Chemical Formula 1C]

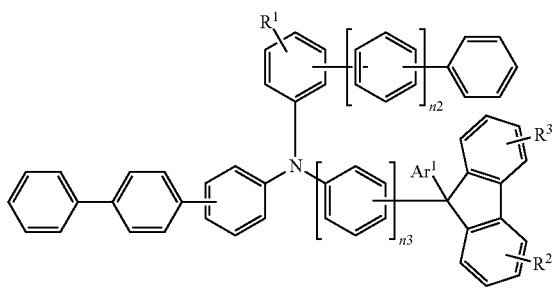

[Chemical Formula 1D]

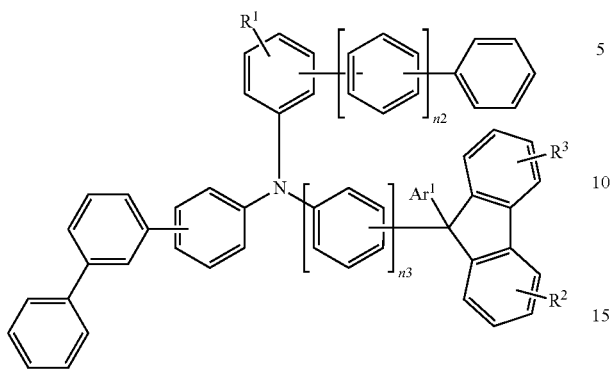

[Chemical Formula 1E]

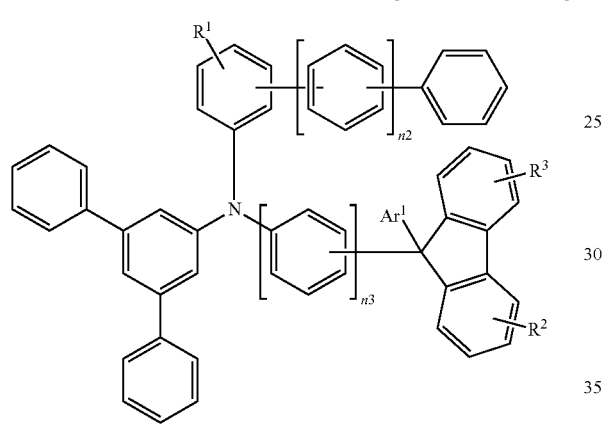

in Chemical Formula 1C to Chemical Formula 1E, $Ar^1$ is a substituted or unsubstituted C6 to C30 aryl group, $R^1$ to $R^3$ are independently hydrogen, deuterium, a cyano group, a halogen, a substituted or unsubstituted C1 to C10 alkyl group, or a phenyl group, n2 is an integer of 0 to 2, and n3 is 1 or 2.

Chemical Formula 1 may be represented by Chemical Formula 1C or Chemical Formula 1D, Chemical Formula 1C is represented by Chemical Formula 1C-1, Chemical Formula 1D is represented by Chemical Formula 1D-1,

[Chemical Formula 1C-1]

[Chemical Formula 1D-1]

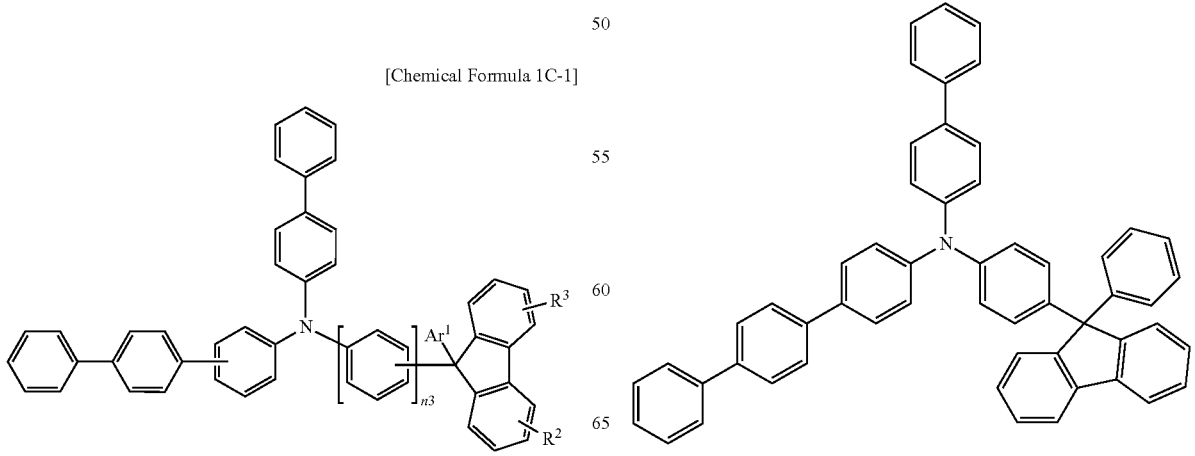

in Chemical Formula 1C-1 and Chemical Formula 1D-1, $Ar^1$ is a substituted or unsubstituted C6 to C20 aryl group, $R^2$ and $R^3$ are independently hydrogen, deuterium, a cyano group, a halogen, a substituted or unsubstituted C1 to C10 alkyl group, or a phenyl group, and n3 is 1 or 2.

$Ar^1$ may be a phenyl group or a biphenyl group.

The compound represented by Chemical Formula 1 may be a compound of Group 1:

[Group 1]

[1]

[2]
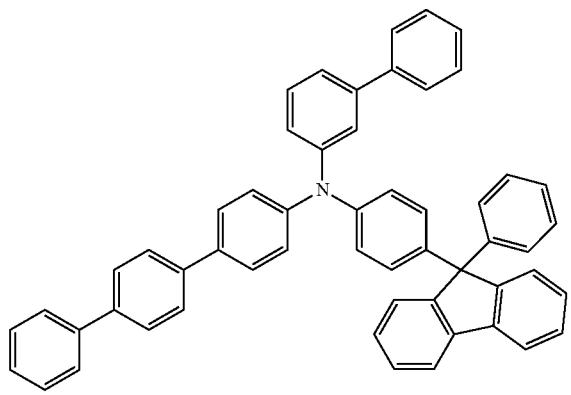
[3]
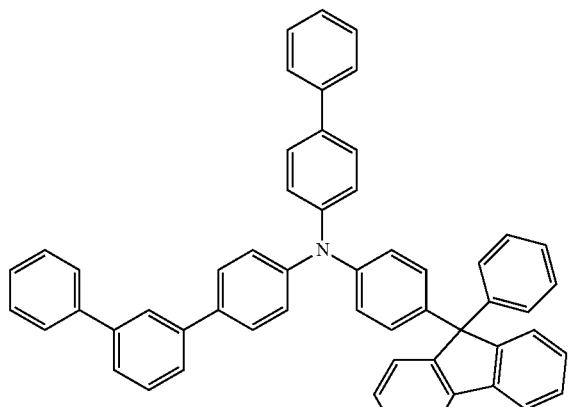
[4]
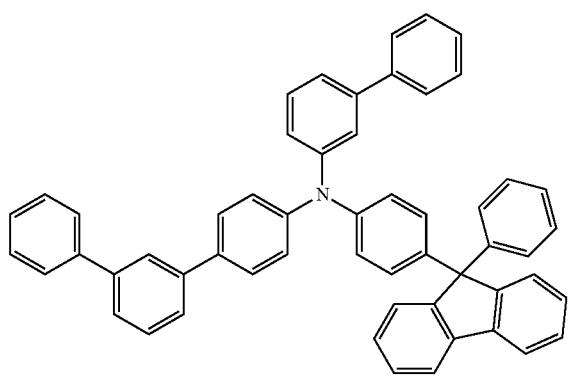
[5]
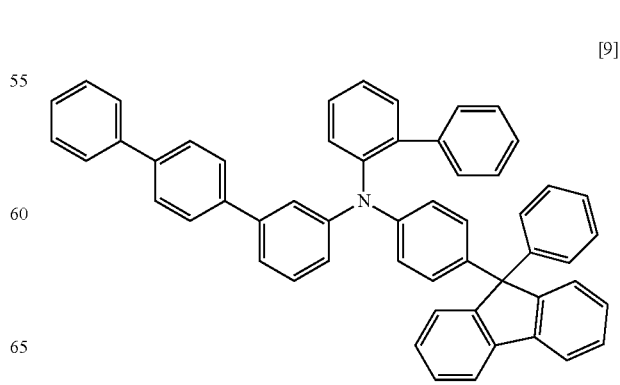
[6]
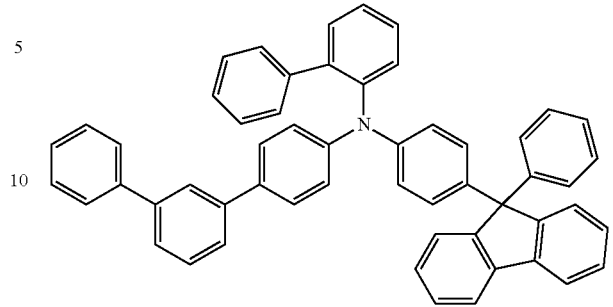
[7]
[8]
[9]

[10]
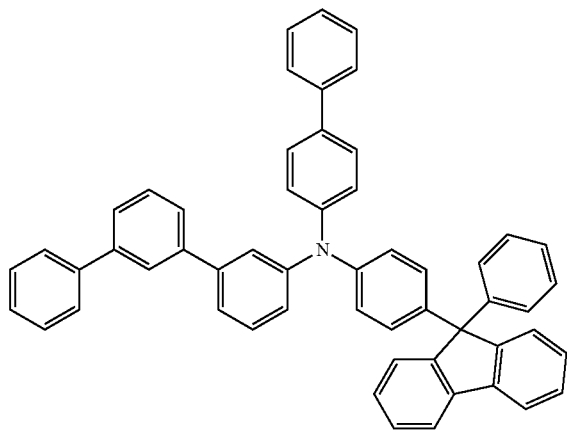
[11]
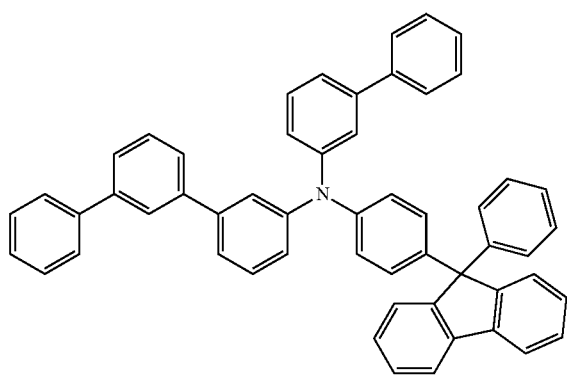
[12]
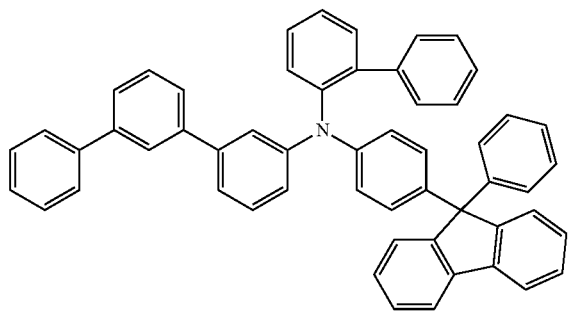
[13]
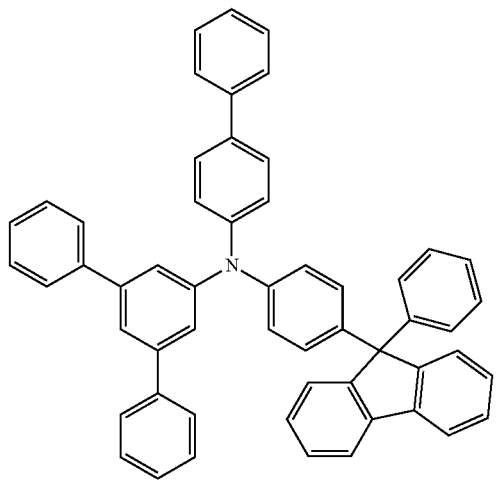
[14]
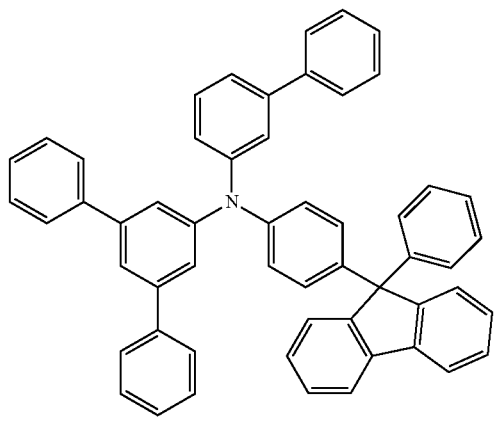
[15]
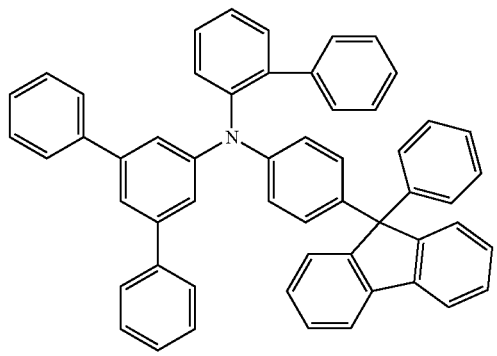

[16]
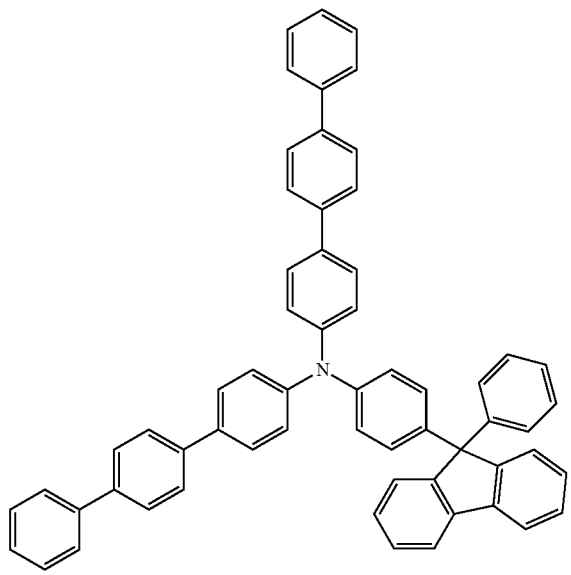
[17]
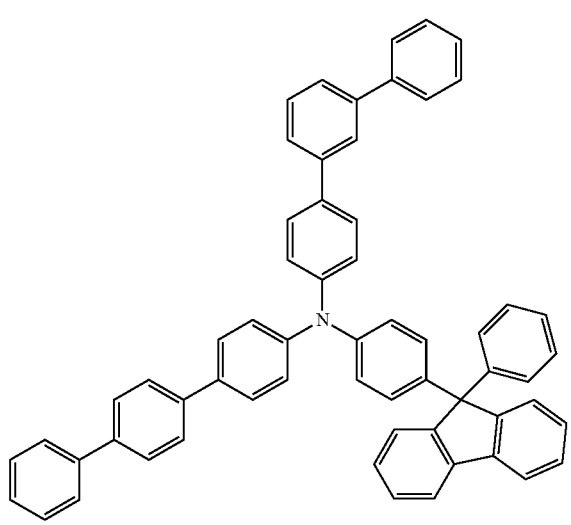
[18]
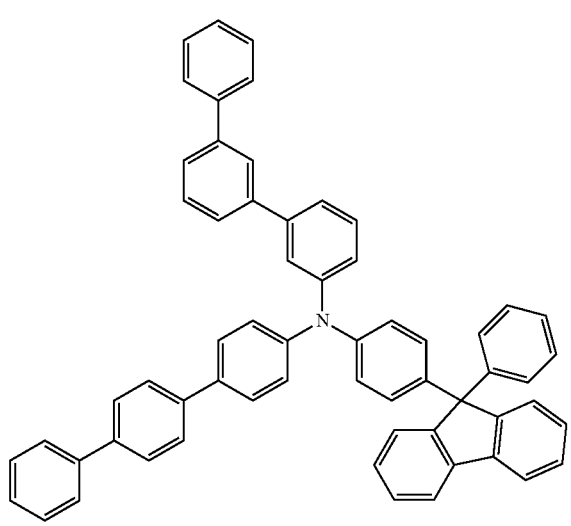
[19]
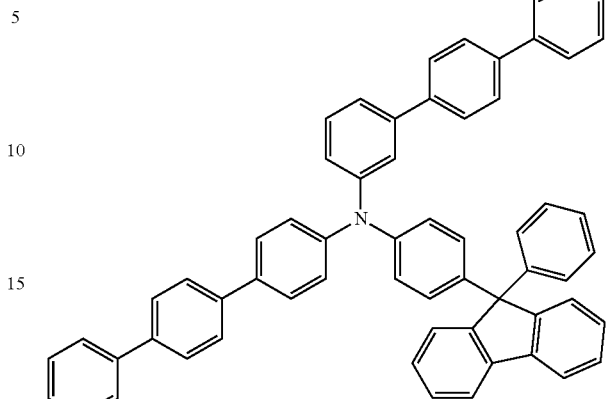
[20]
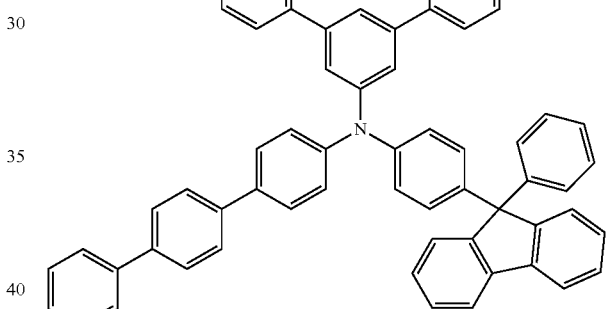
[21]
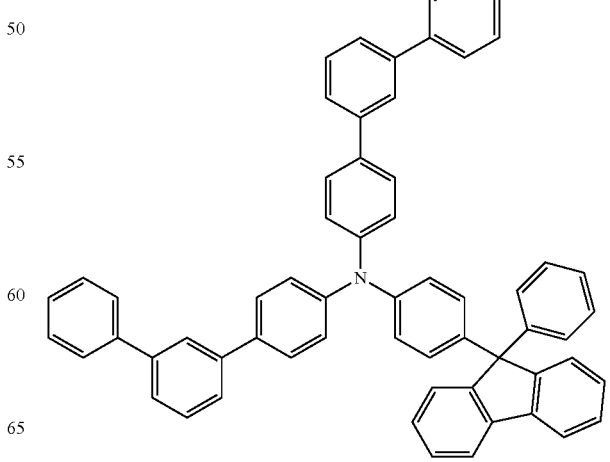

[22]
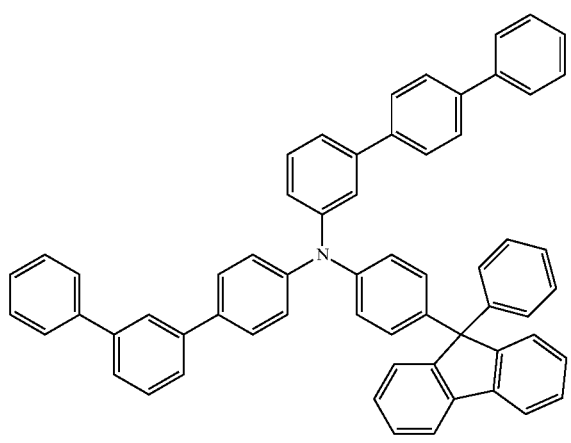
[25]
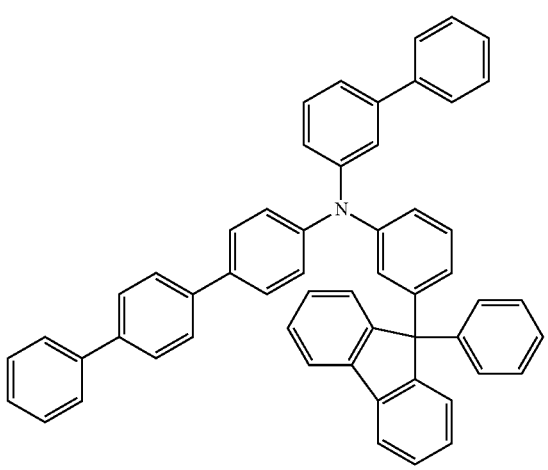
[23]
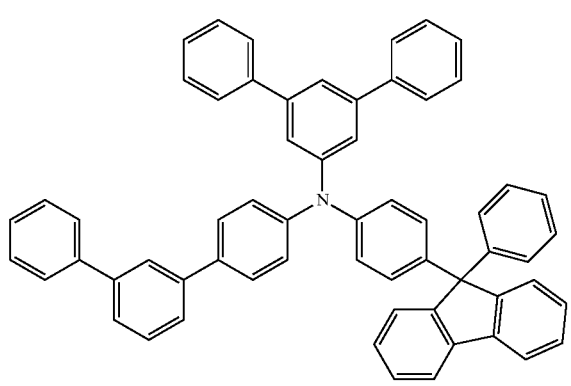
[26]
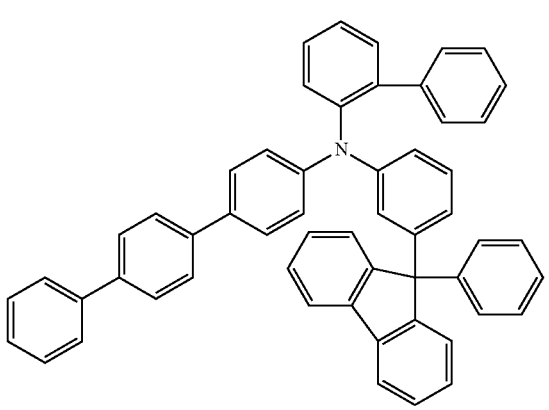
[24]
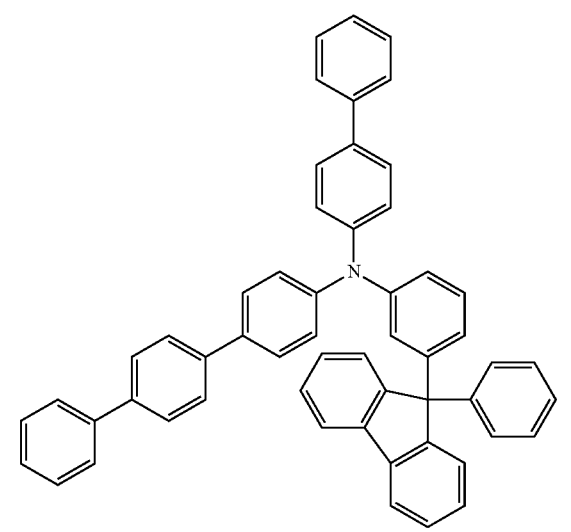
[27]
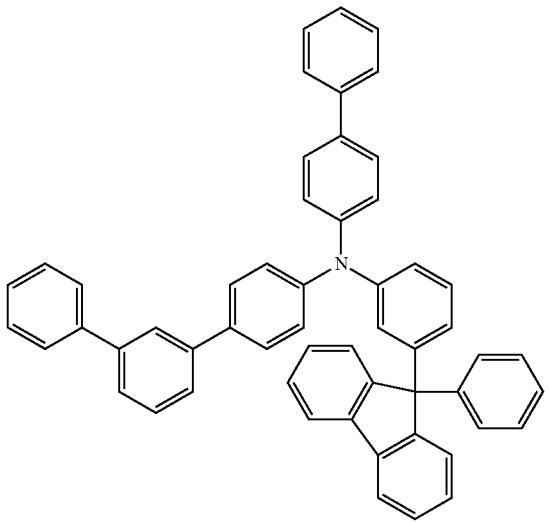

[28]
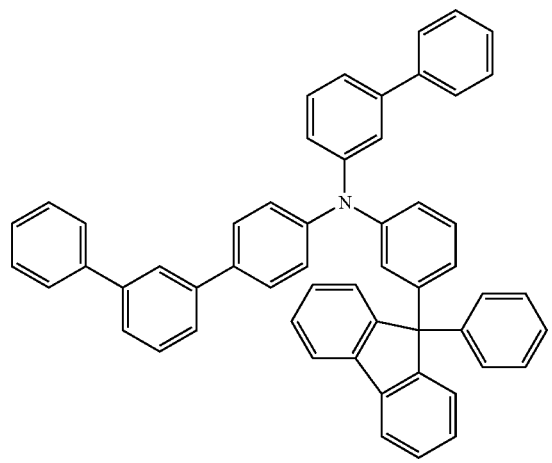
[29]
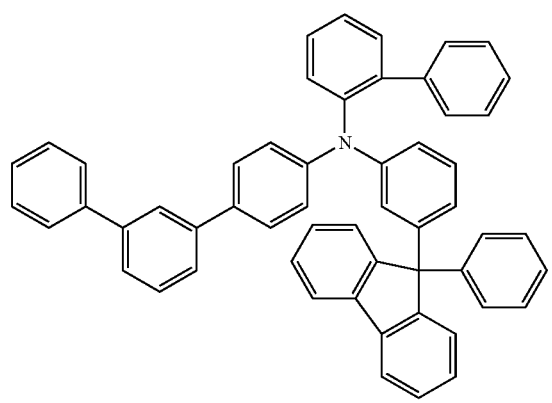
[30]
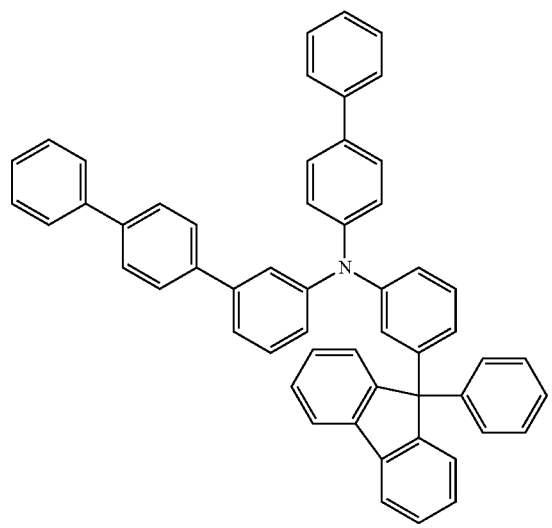
[31]
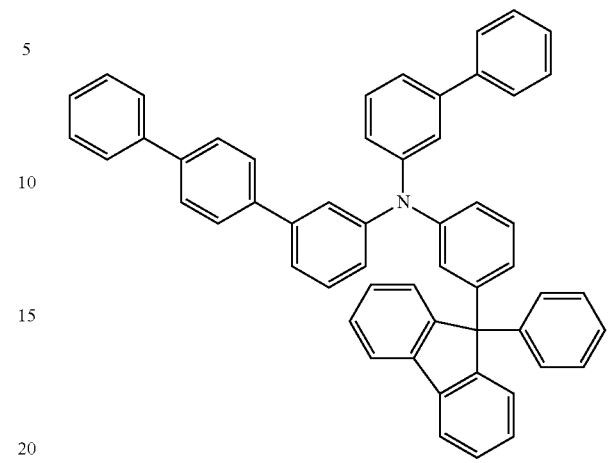
[32]
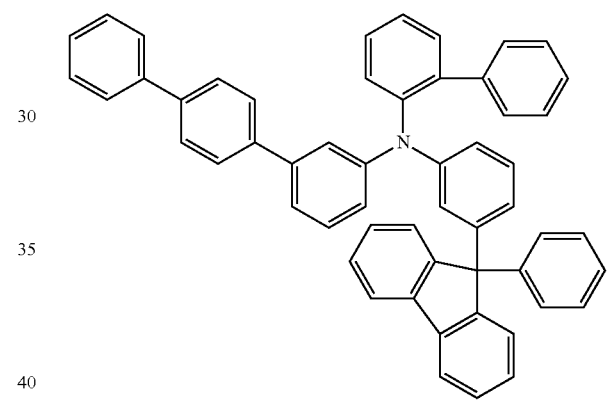
[33]
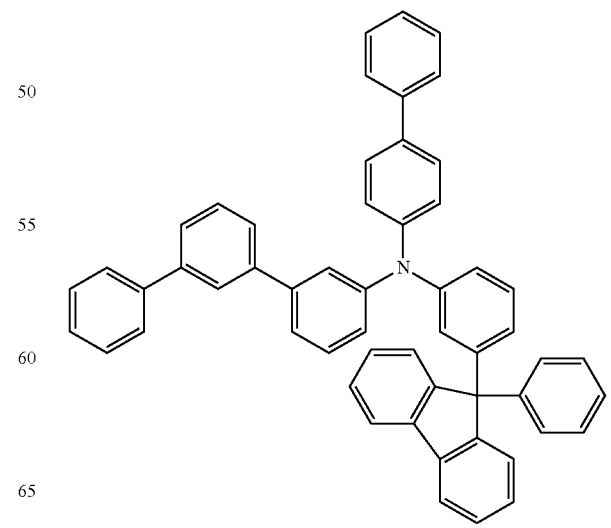

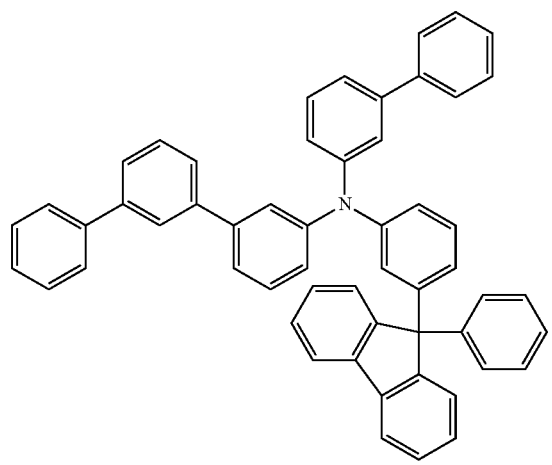
[34]
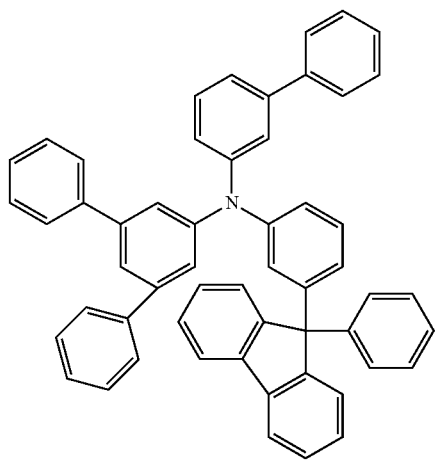
[37]
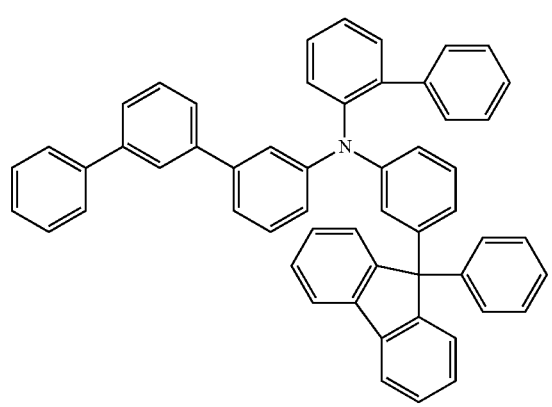
[35]
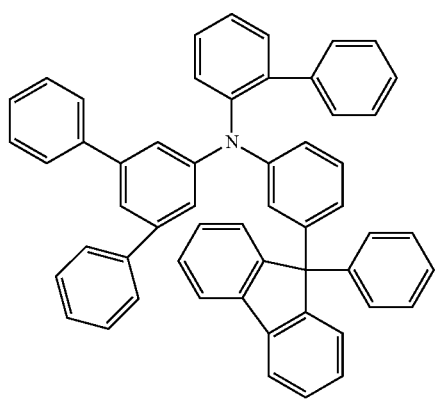
[38]
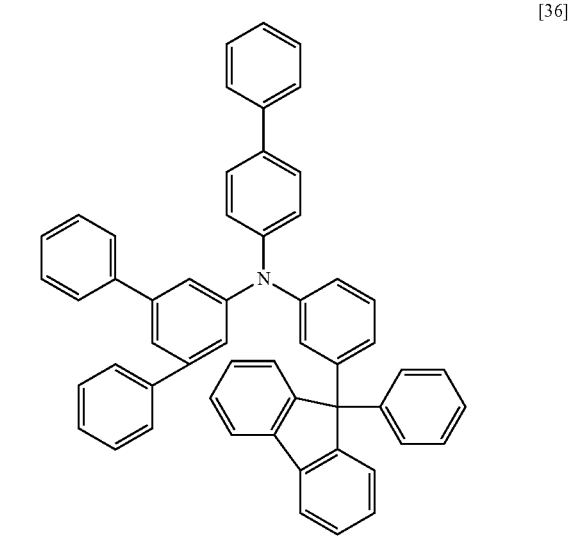
[36]
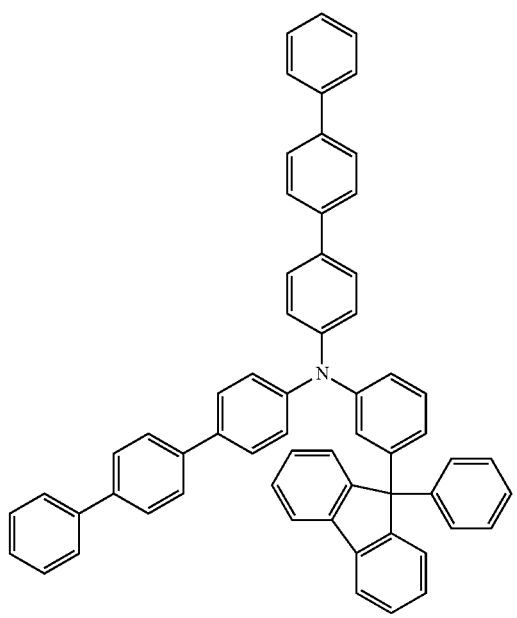
[39]

[40]
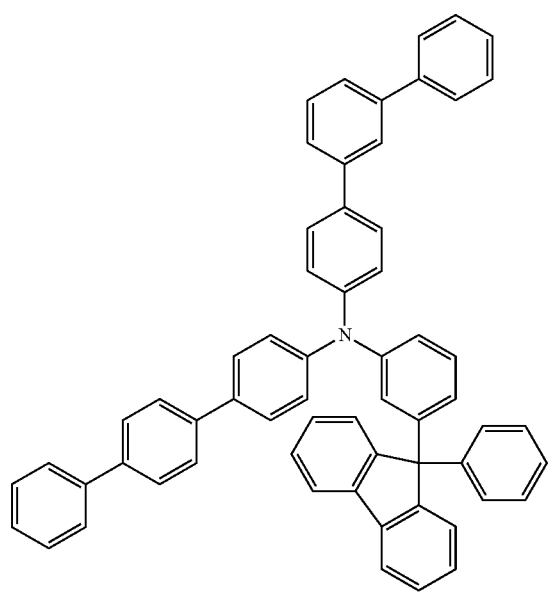
[41]
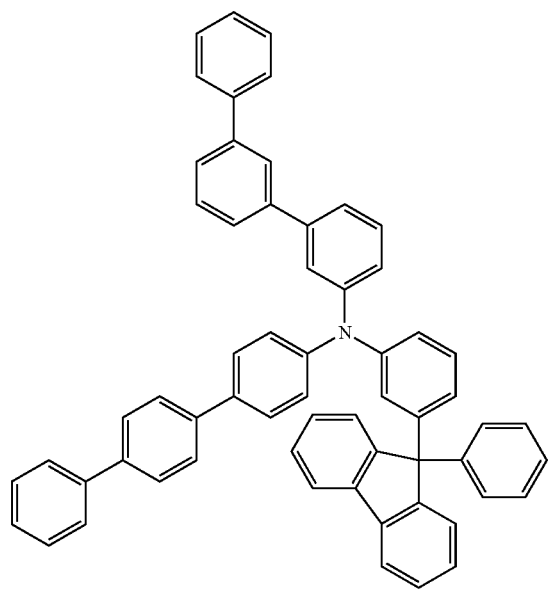
[42]
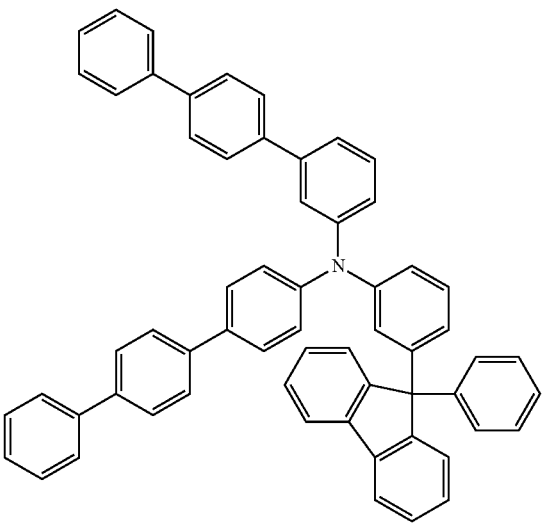
[43]
[44]

[45]

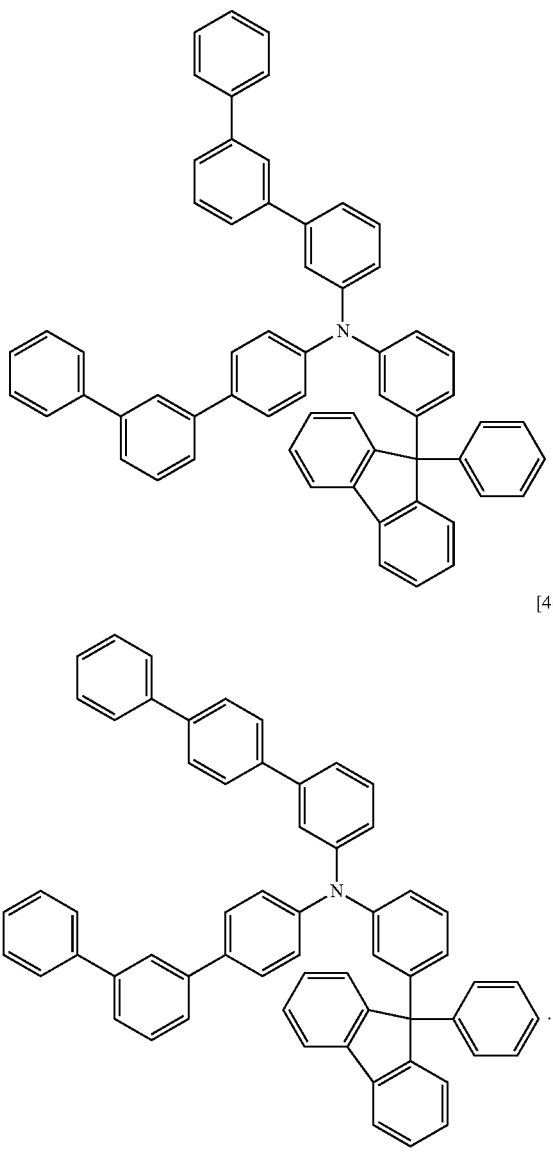

[46]

The embodiments may be realized by providing an organic optoelectronic device including an anode and a cathode facing each other; and at least one organic layer between the anode and the cathode, wherein the at least one organic layer includes the compound for an organic optoelectronic device according to an embodiment.

The at least one organic layer may include a light emitting layer, and a hole auxiliary layer between the anode and the light emitting layer, and the hole auxiliary layer may include the compound for an organic optoelectronic device.

The hole auxiliary layer may include a hole transport layer, and a hole transport auxiliary layer between the light emitting layer and the hole transport layer, and the hole transport auxiliary layer may include the compound for an organic optoelectronic device.

The embodiments may be realized by providing a display device including the organic optoelectronic device according to an embodiment.

BRIEF DESCRIPTION OF THE DRAWING

Features will become apparent to those of skill in the art by describing in detail exemplary embodiments with reference to the attached drawing in which:

The FIGURE is a cross-sectional view showing an organic light emitting diode according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. It will also be understood that when a layer or element is referred to as being "on" another layer or element, it can be directly on the other layer or substrate, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples, "substituted" refers to replacement of at least one hydrogen of a substituent or a compound by deuterium, a C1 to C20 alkyl group, a C6 to C30 aryl group, or a C2 to C30 heteroaryl group. In addition, in specific examples, "substituted" refers to replacement of at least one hydrogen of a substituent or a compound by deuterium, a C1 to C5 alkyl group, a C6 to C18 aryl group, a dibenzofuranyl group, a dibenzothiophenyl group, or a carbazolyl group. In addition, in specific examples, "substituted" refers to replacement of at least one hydrogen of a substituent or a compound by a C6 to C18 aryl group. In addition, in specific examples, "substituted" refers to replacement of at least one hydrogen of a substituent or a compound by a phenyl group, a biphenyl group, a terphenyl group, a naphthyl group, an anthracenyl group, a phenanthrenyl group, or a triphenylene group.

As used herein, when a definition is not otherwise provided, "hetero" refers to one including one to three heteroatoms selected from N, O, S, P, and Si, and remaining carbons in one functional group.

As used herein, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quaterphenyl group, and the like, and a group in which two or more hydrocarbon aromatic moieties are fused directly or indirectly to provide a non-aromatic fused ring, for example a fluorenyl group, and the like.

The aryl group may include a monocyclic, polycyclic or fused ring polycyclic (i.e., rings sharing adjacent pairs of carbon atoms) functional group.

As used herein, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, a substituted or unsubstituted dibenzothiophenyl group, or a combination thereof.

In the present specification, hole characteristics refer to an ability to donate an electron to form a hole when an electric field is applied and that a hole formed in the anode may be easily injected into the light emitting layer and transported in the light emitting layer due to conductive characteristics according to the highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to the lowest unoccupied molecular orbital (LUMO) level.

Hereinafter, a compound for an organic optoelectronic device according to an embodiment is described. In an implementation, the compound for an organic optoelectronic device may be represented by Chemical Formula 1.

[Chemical Formula 1]

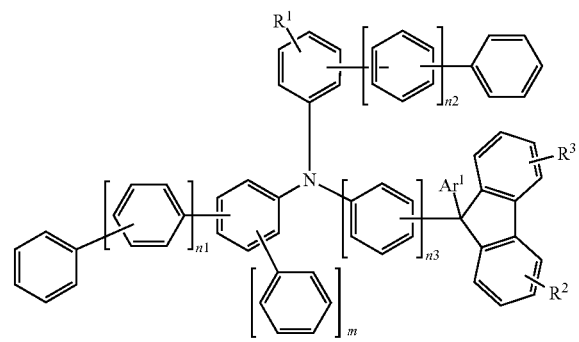

In Chemical Formula 1, $Ar^1$ may be or may include, e.g., a substituted or unsubstituted C6 to C30 aryl group.

$R^1$ to $R^3$ may each independently be or include, e.g., hydrogen, deuterium, a cyano group, a halogen, a substituted or unsubstituted C1 to C10 alkyl group, or a phenyl group.

n1 and m may each independently be, e.g., 0 or 1. n1+m=1.

n2 may be, e.g., an integer of 0 to 2.

n3 may be, e.g., 1 or 2.

The compound represented by Chemical Formula 1 may have a structure in which the amine moiety (connected to position 9 of the fluorene moiety) includes at least one terphenyl group thereon.

A shallower HOMO energy level may be obtained by an amine core including a 9-fluorene group and a terphenyl groups, and long life-span/low voltage driving characteristics of the organic light emitting diode to which it is applied by improving the electron and hole transport characteristics of the amine may be realized.

In an implementation, Chemical Formula 1 may be represented by Chemical Formula 1A or Chemical Formula 1B.

[Chemical Formula 1A]

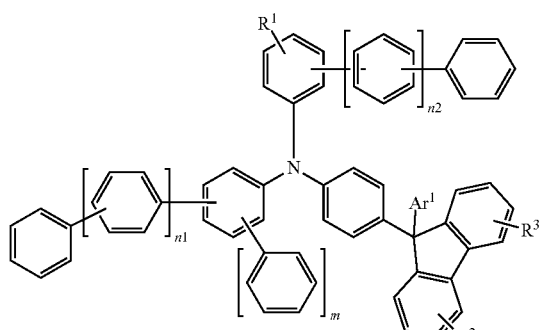

[Chemical Formula 1B]

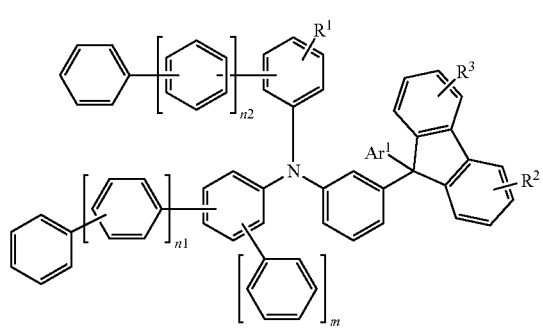

In Chemical Formula 1A and Chemical Formula 1B, $Ar^1$, $R^1$ to $R^3$, n1, n2, and m may be defined the same as those of Chemical Formula 1.

In an implementation, Chemical Formula 1 may be represented by one of Chemical Formula 1C to Chemical Formula 1E.

[Chemical Formula 1C]

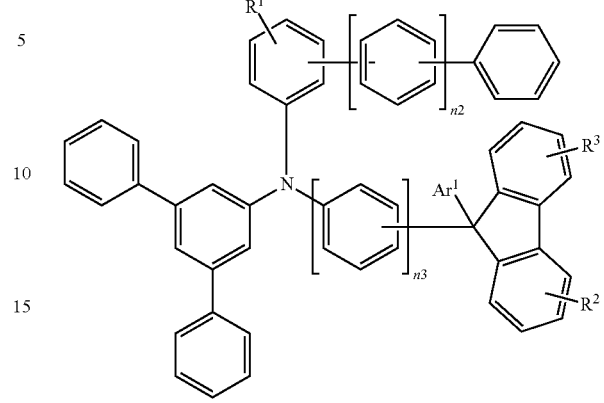

[Chemical Formula 1D]

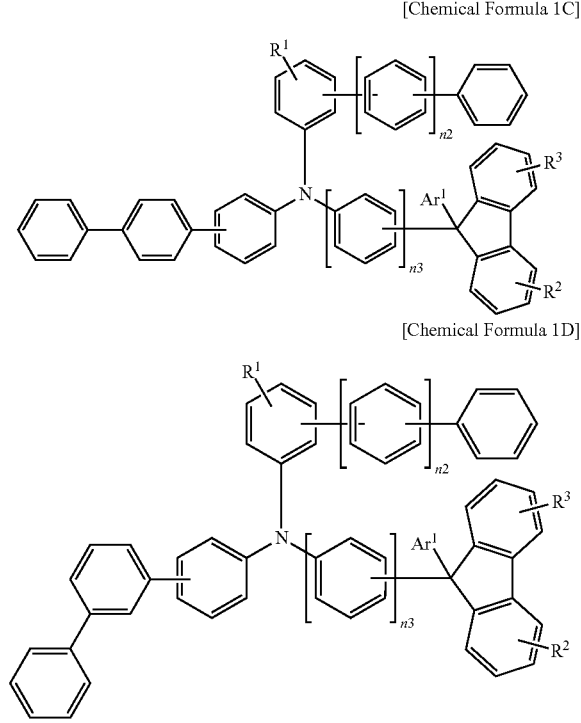

[Chemical Formula 1E]

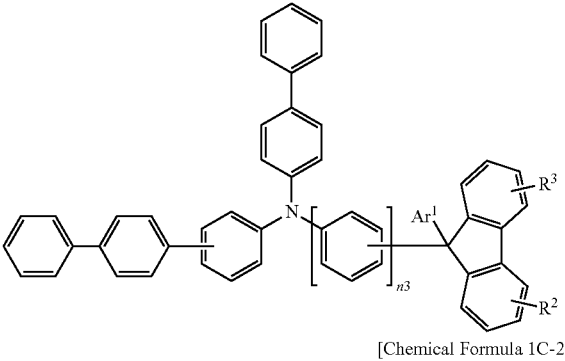

In Chemical Formula 1C to Chemical Formula 1E, $Ar^1$, $R^1$ to $R^3$, n2, and n3 may be defined the same as those of Chemical Formula 1.

In an implementation, Chemical Formula 1C may be represented by one of Chemical Formula 1C-1 to Chemical Formula 1C-8.

[Chemical Formula 1C-1]

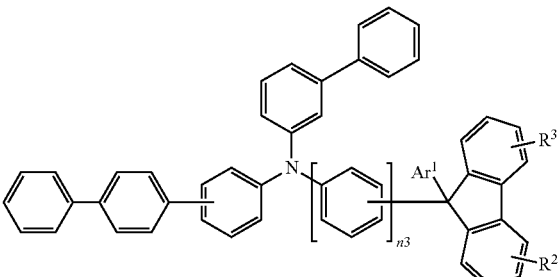

[Chemical Formula 1C-2]

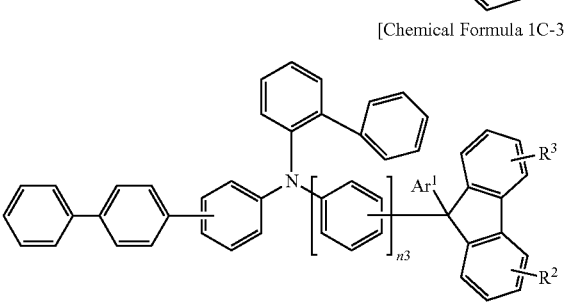

[Chemical Formula 1C-3]

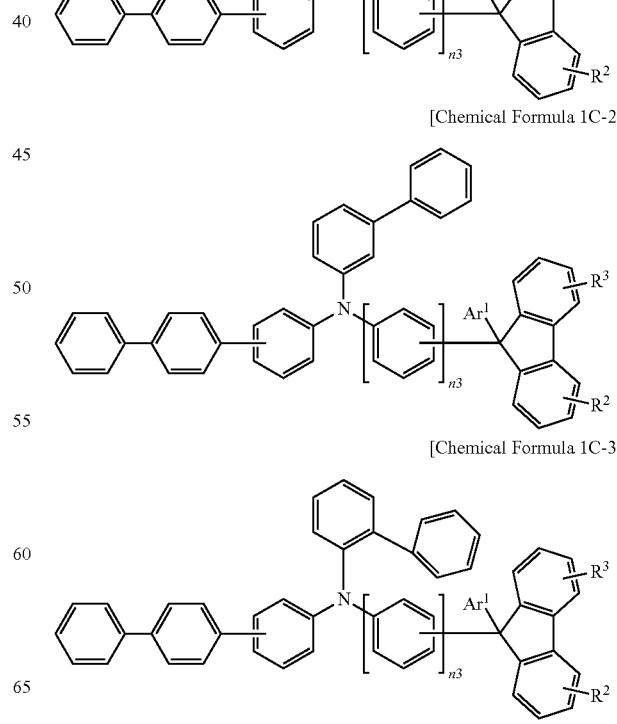

[Chemical Formula 1C-4]
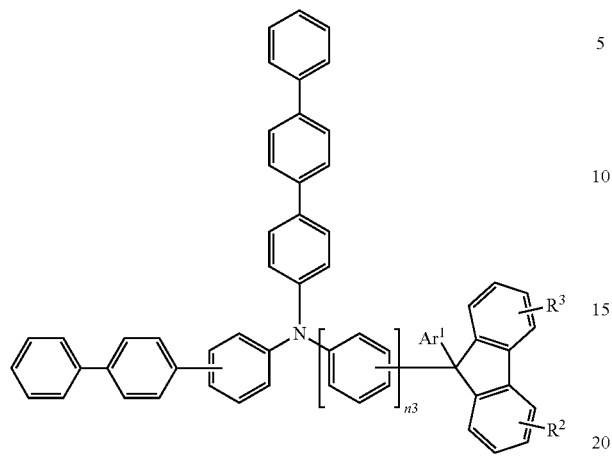
[Chemical Formula 1C-5]
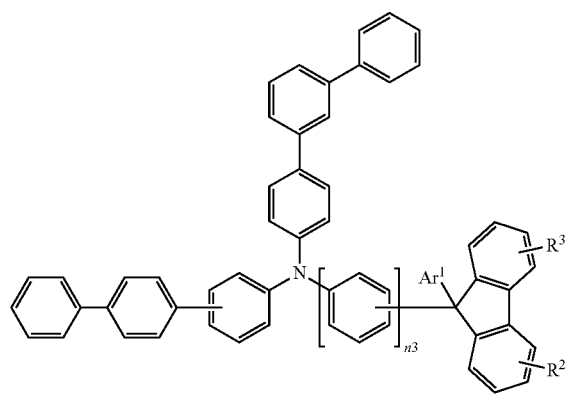
[Chemical Formula 1C-6]
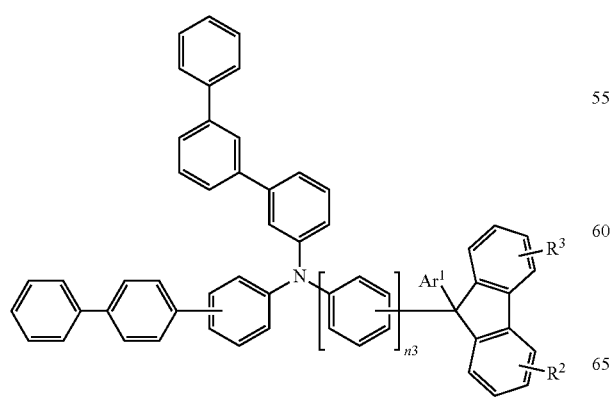
[Chemical Formula 1C-7]
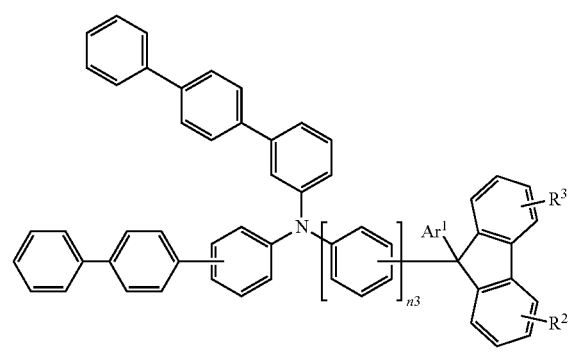
[Chemical Formula 1C-8]
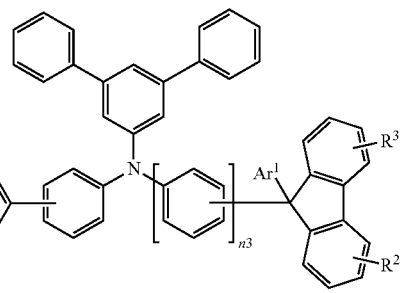
In Chemical Formula 1C-1 to Chemical Formula 1C-8, Ar$^1$, R$^2$, R$^3$, and n3 may be defined the same as those of Chemical Formula 1.
In an implementation, Chemical Formula 1D may be represented by one of Chemical Formula 1D-1 to Chemical Formula 1D-8.
[Chemical Formula 1D-1]
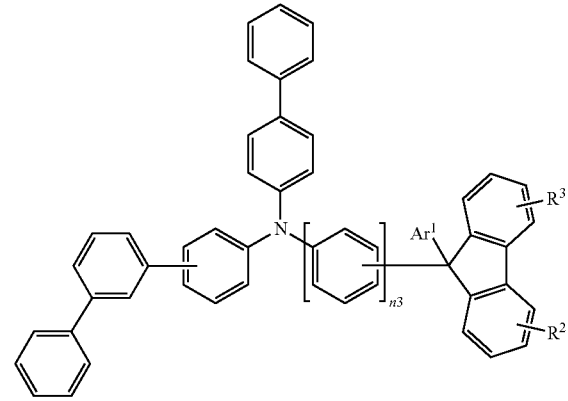

[Chemical Formula 1D-2]
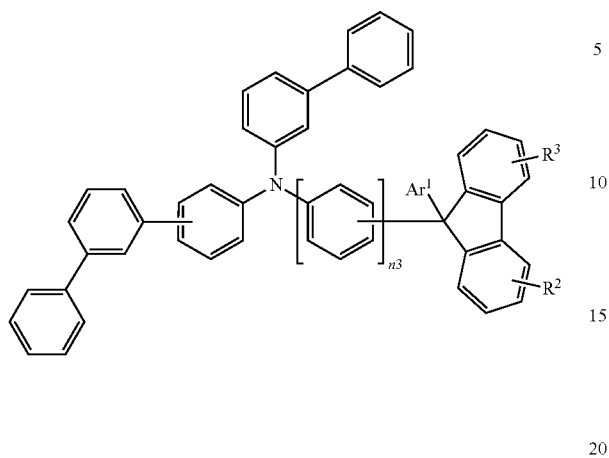
[Chemical Formula 1D-3]
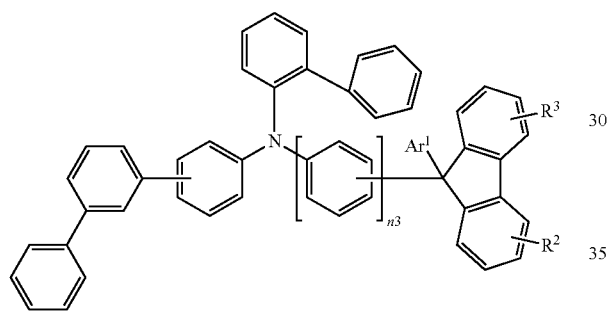
[Chemical Formula 1D-4]
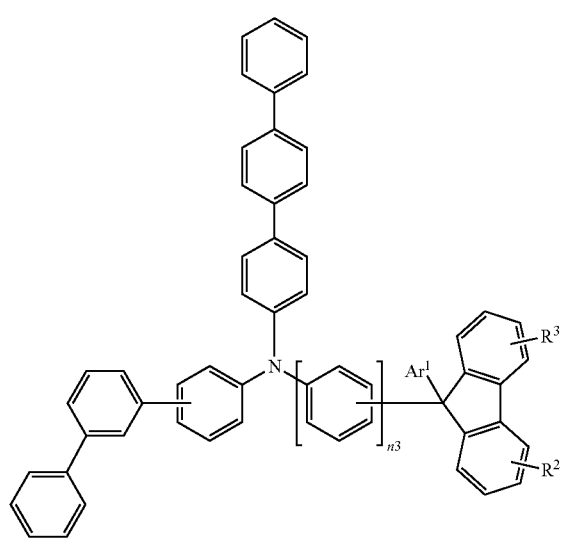
[Chemical Formula 1D-5]
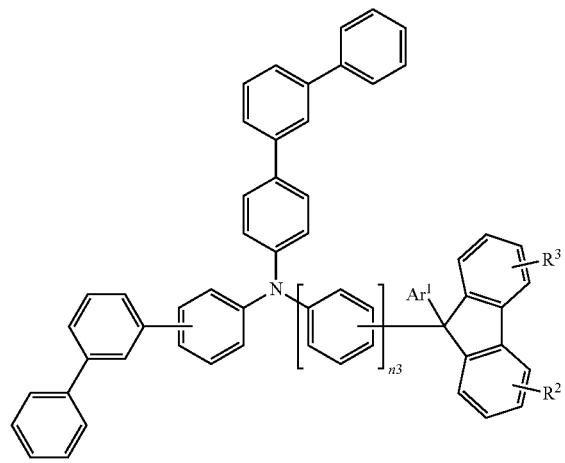
[Chemical Formula 1D-6]
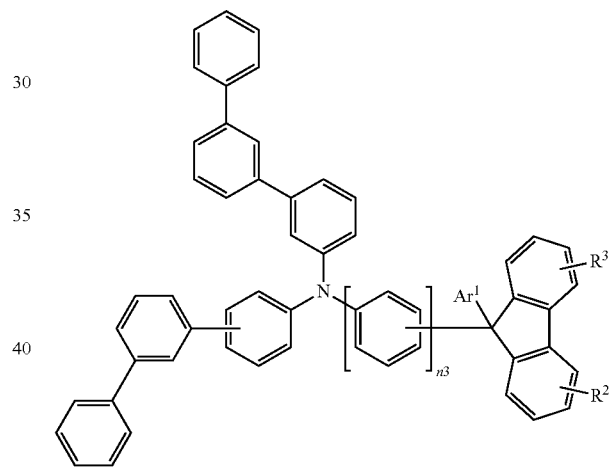
[Chemical Formula 1D-7]
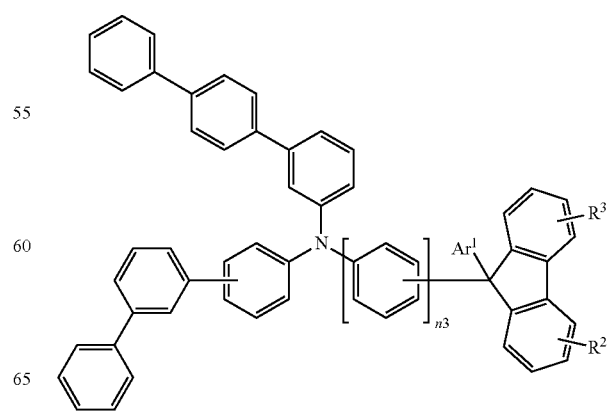

[Chemical Formula 1D-8]
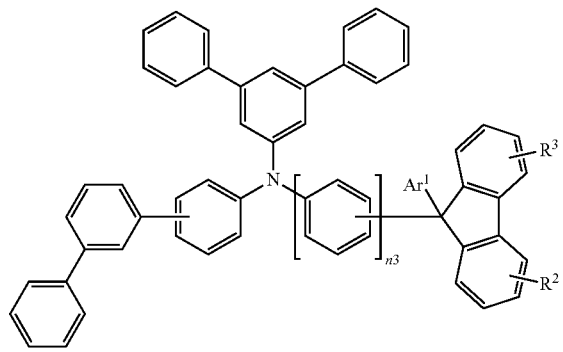
In Chemical Formula 1D-1 to Chemical Formula 1D-8, $Ar^1$, $R^2$, $R^3$, and n3 may be defined the same as those of Chemical Formula 1.
In an implementation, Chemical Formula 1E may be represented by one of Chemical Formula 1E-1 to Chemical Formula 1E-8.
[Chemical Formula 1E-1]
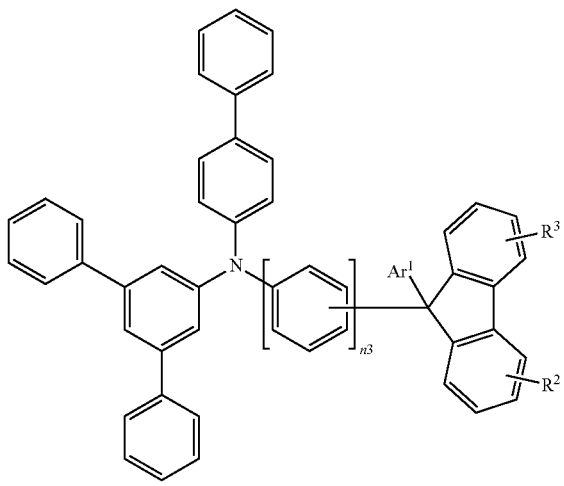
[Chemical Formula 1E-2]
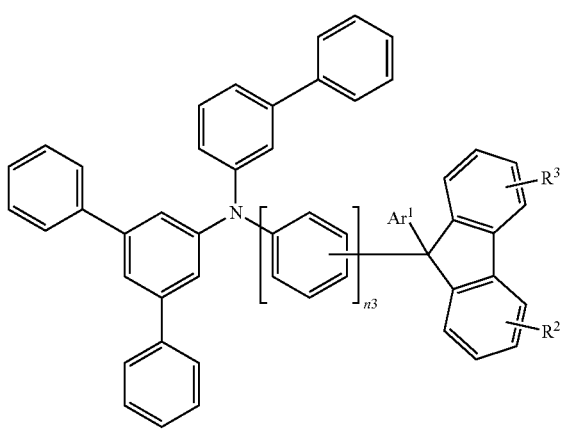
[Chemical Formula 1E-3]
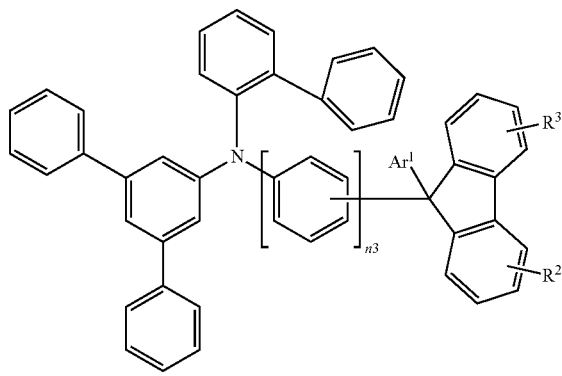
[Chemical Formula 1E-4]
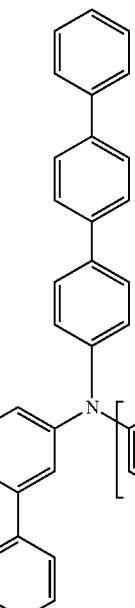
[Chemical Formula 1E-5]
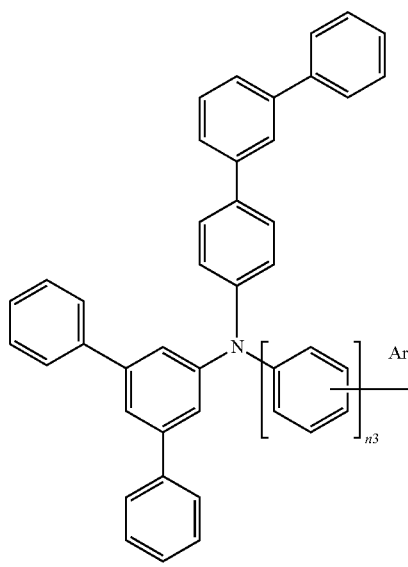

[Chemical Formula 1E-6]

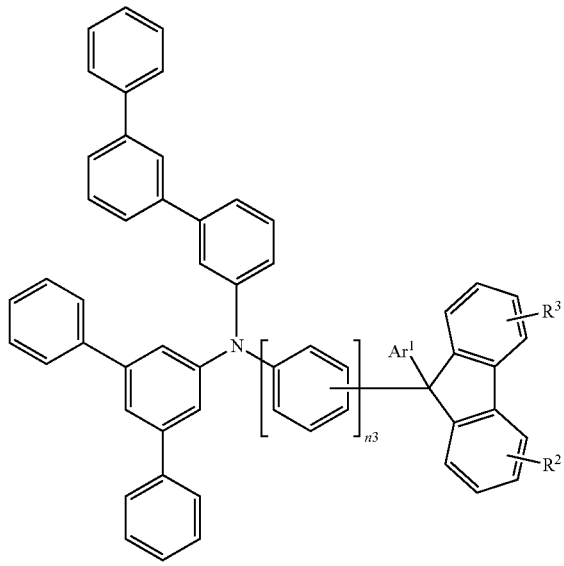

[Chemical Formula 1E-7]

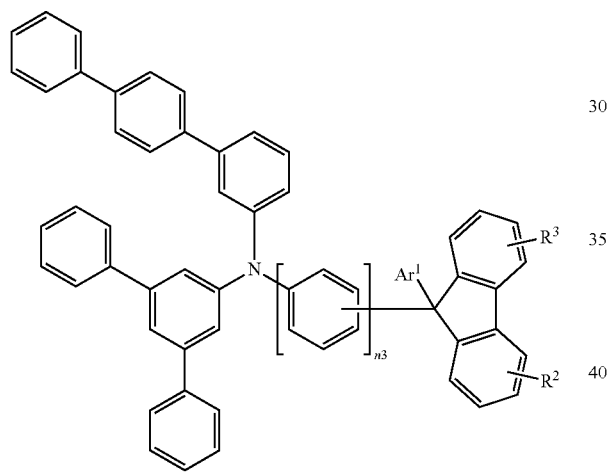

[Chemical Formula 1E-8]

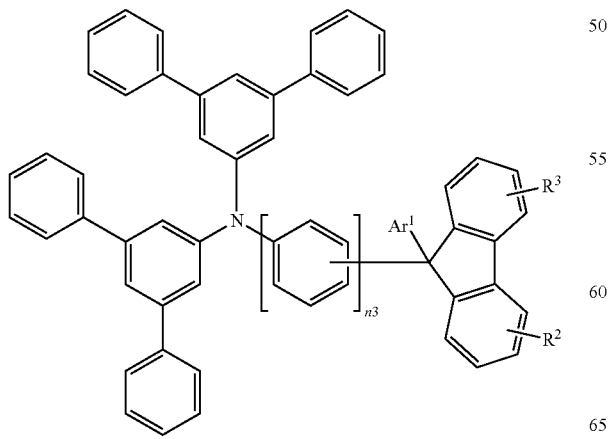

In Chemical Formula 1E-1 to Chemical Formula 1E-8, $Ar^1$, $R^2$, $R^3$, and n3 may be defined the same as those of Chemical Formula 1.

In an implementation, the compound for an organic optoelectronic device may be represented by Chemical Formula 1C-1 or 1D-1.

In an implementation, $Ar^1$ in Chemical Formula 1 may be, e.g., a substituted or unsubstituted C6 to C20 aryl group.

In an implementation, $Ar^1$ in Chemical Formula 1 may be a phenyl group or a biphenyl group.

In an implementation, $R^1$ to $R^3$ in Chemical Formula 1 may each independently be or include, e.g., hydrogen, deuterium, a cyano group, a halogen group, a substituted or unsubstituted C1 to C10 alkyl group, or a phenyl group. In an implementation, $R^1$ to $R^3$ in Chemical Formula 1 may each independently be or include, e.g., hydrogen, substituted or an unsubstituted C1 to C5 alkyl group, or a phenyl group.

In an implementation, $R^1$ may be, e.g., hydrogen or a substituted or an unsubstituted phenyl group, and $R^2$ and $R^3$ may be hydrogen.

In an implementation, the compound for an organic optoelectronic device may be a compound of Group 1.

[Group 1]

[1]

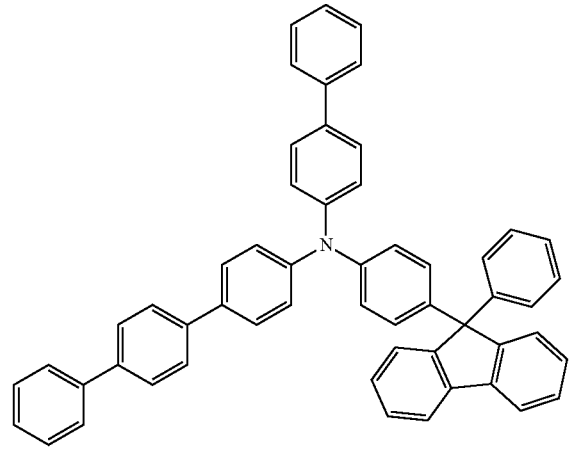

[2]

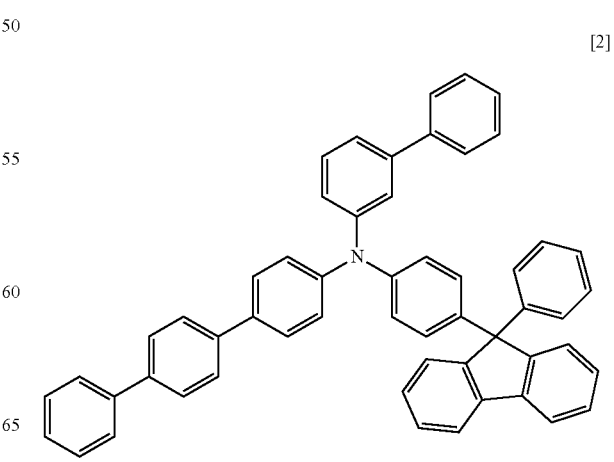

[3]
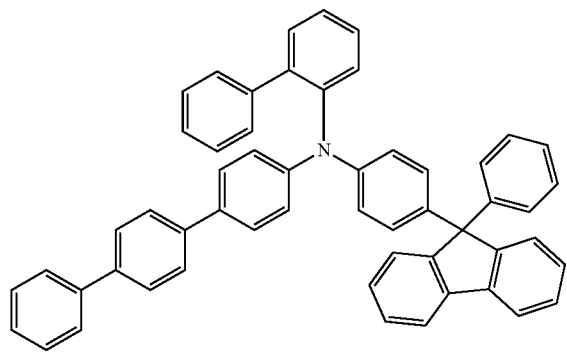
[4]
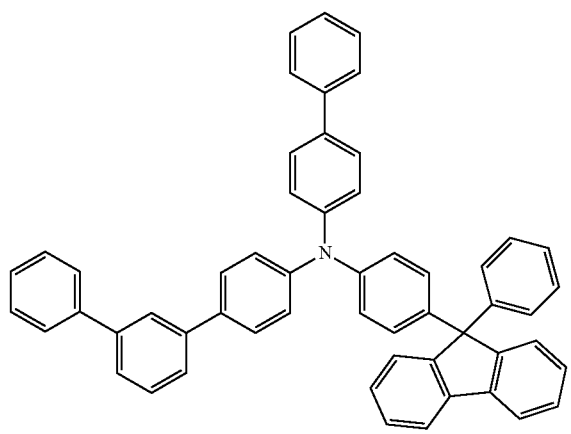
[5]
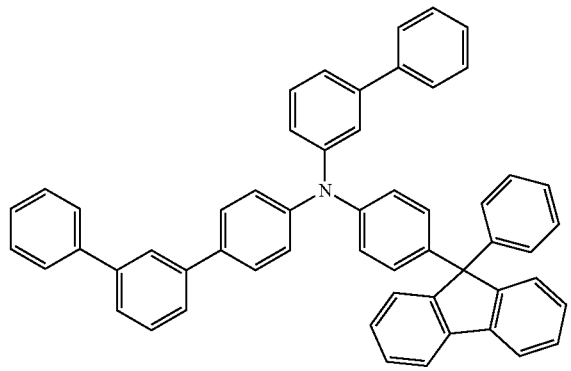
[6]
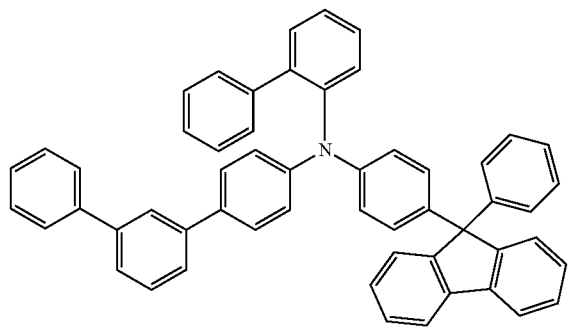
[7]
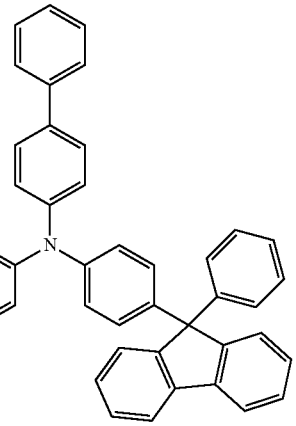
[8]
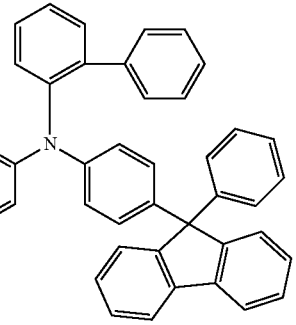
[9]
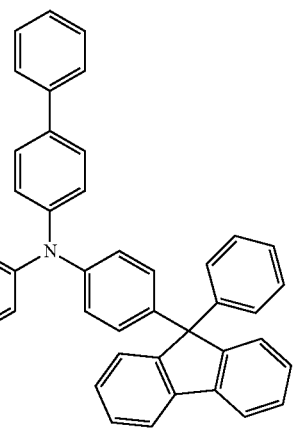
[10]

[11]
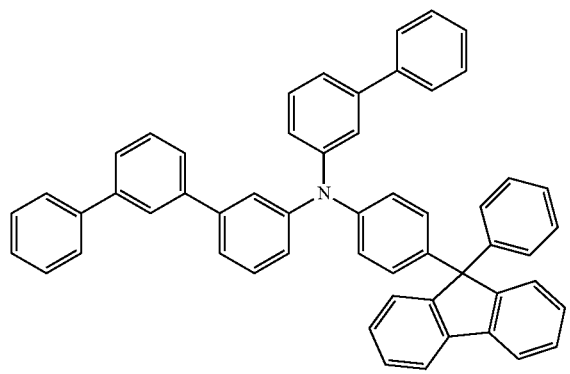
[12]
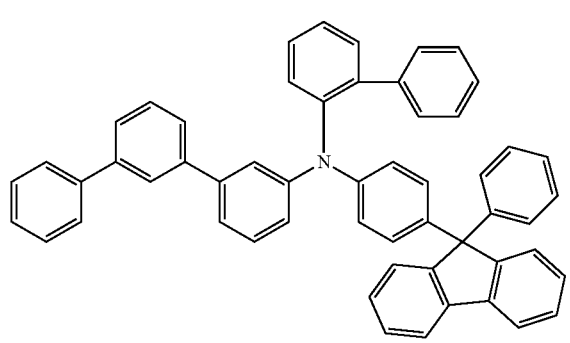
[13]
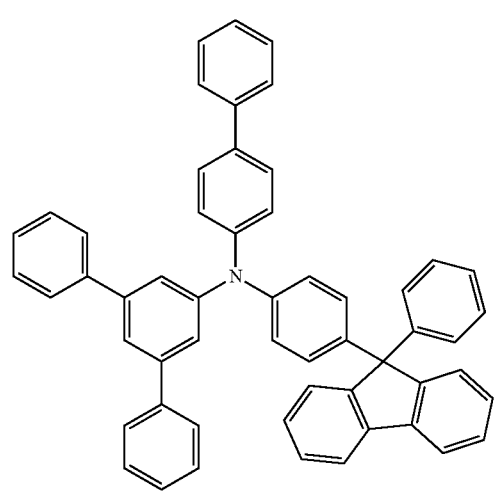
[14]
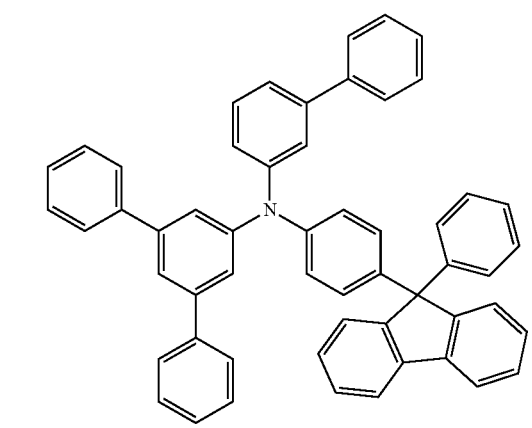
[15]
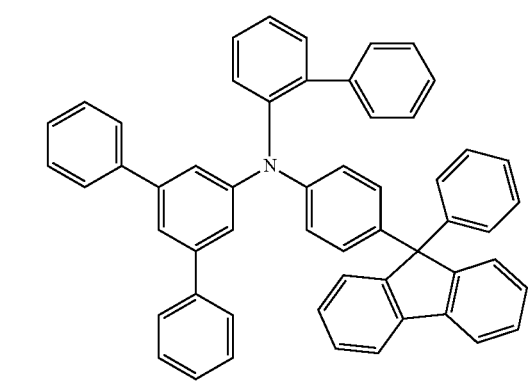
[16]
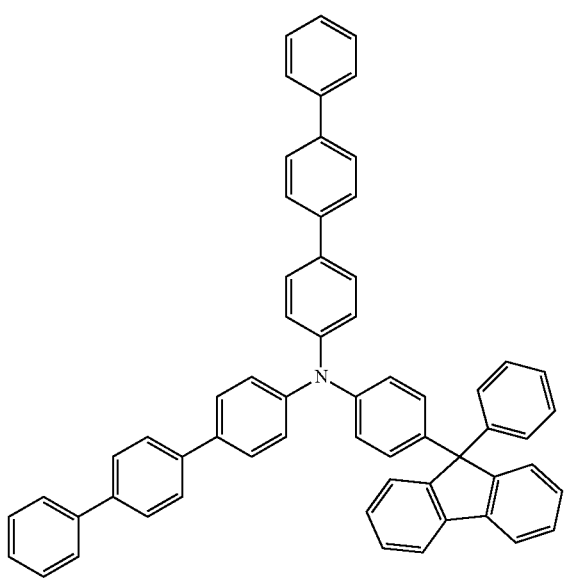

37
-continued
[17]
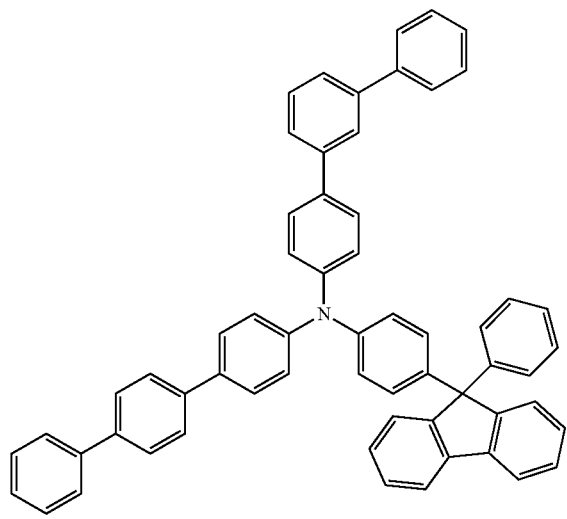
[18]
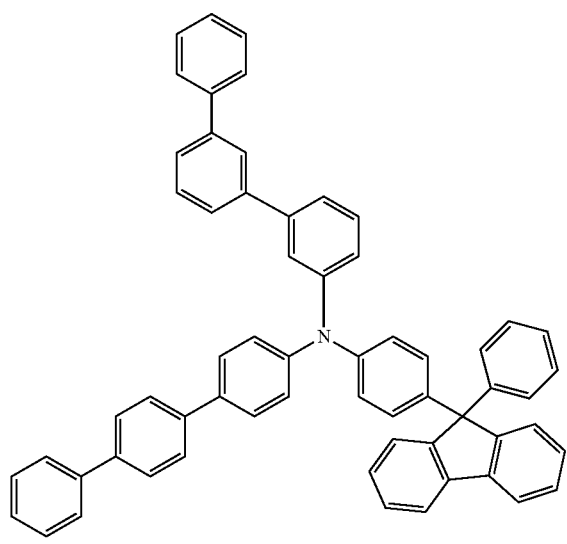
[19]
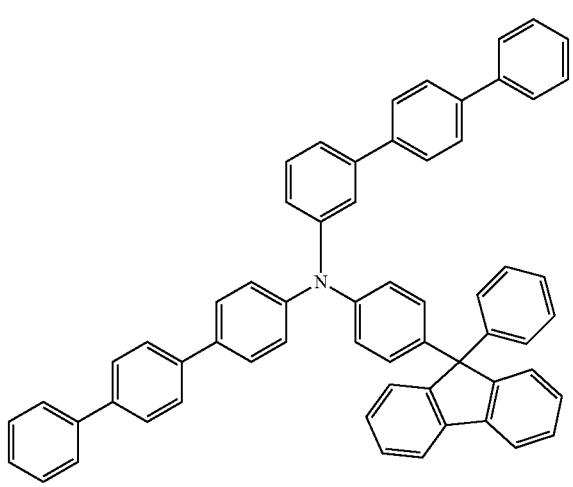
38
-continued
[20]
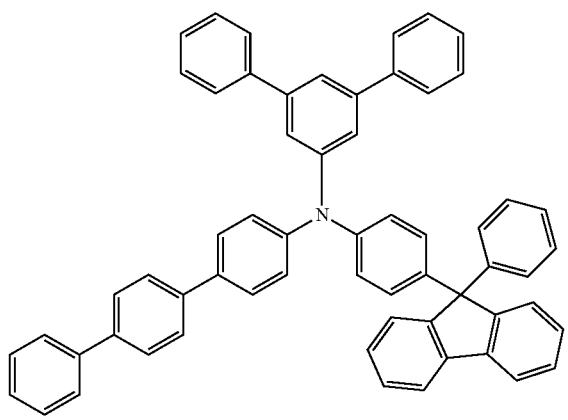
[21]
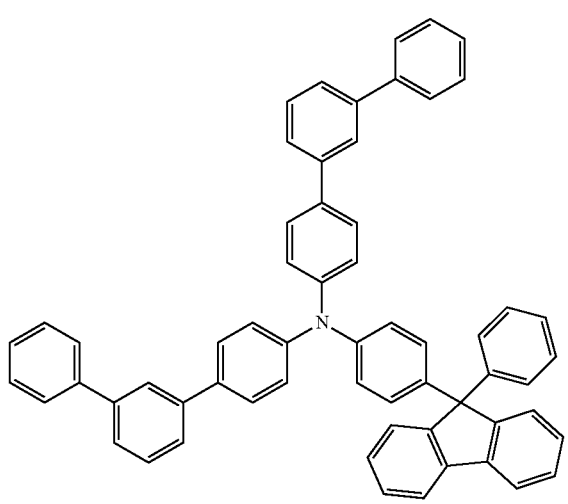
[22]
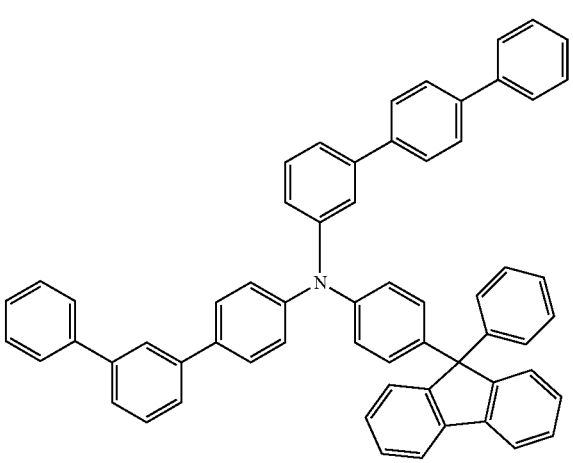

[23]
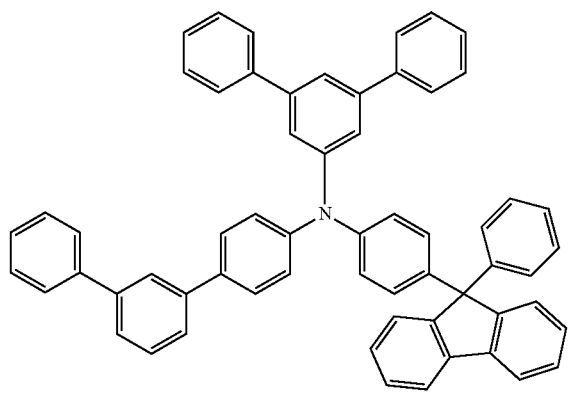
[24]
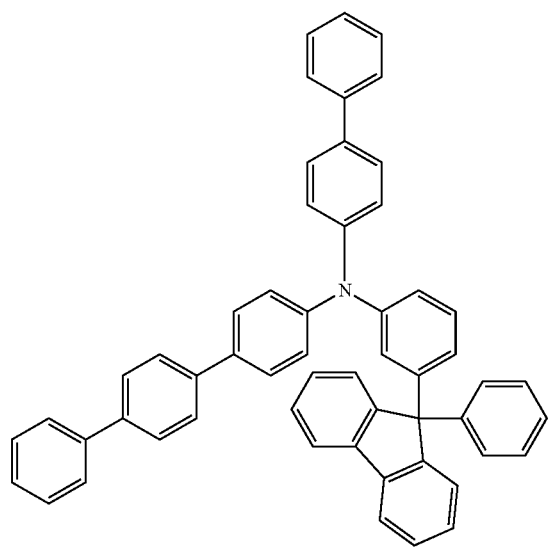
[25]
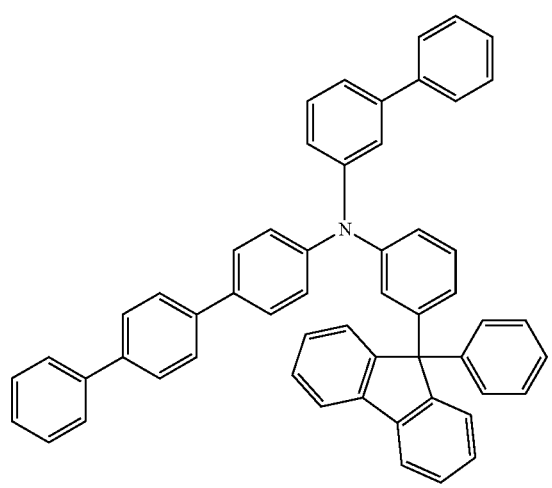
[26]
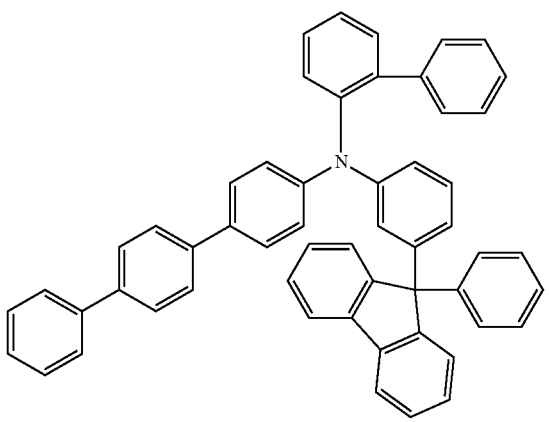
[27]
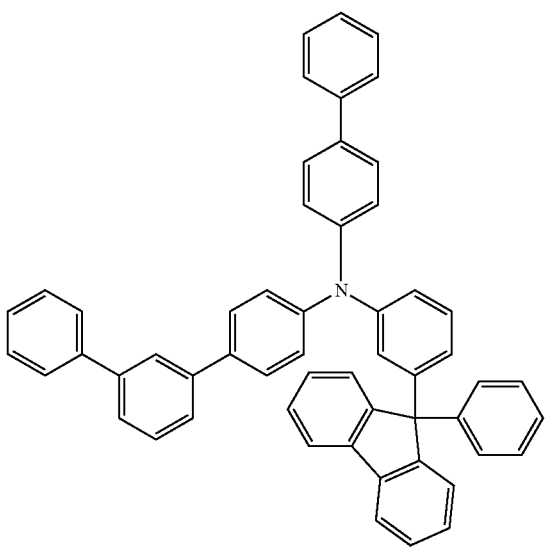
[28]
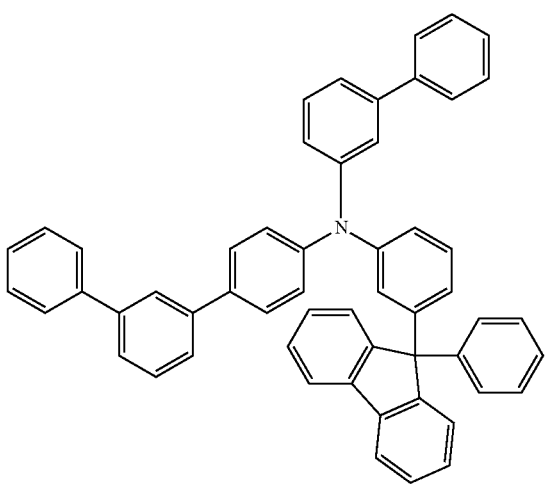

[29]
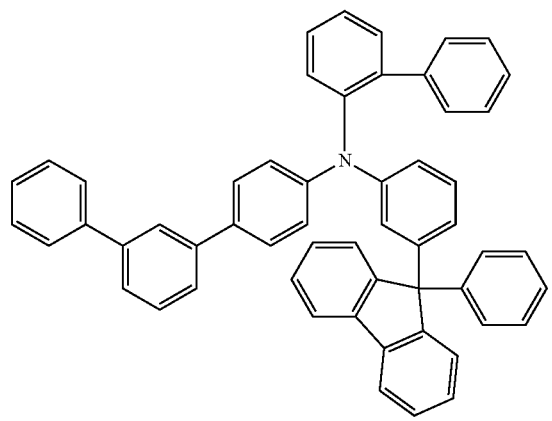
[30]
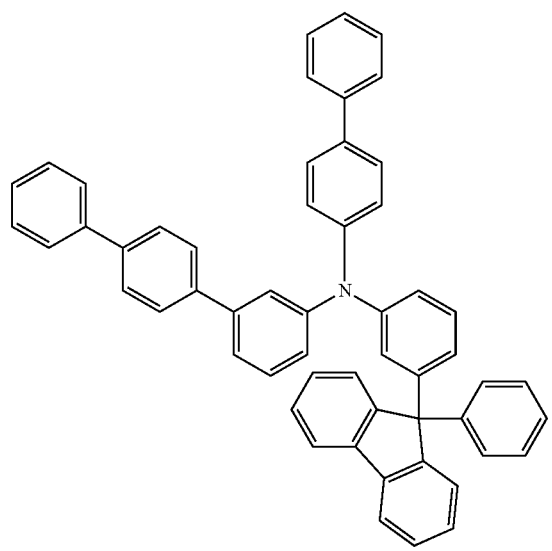
[31]
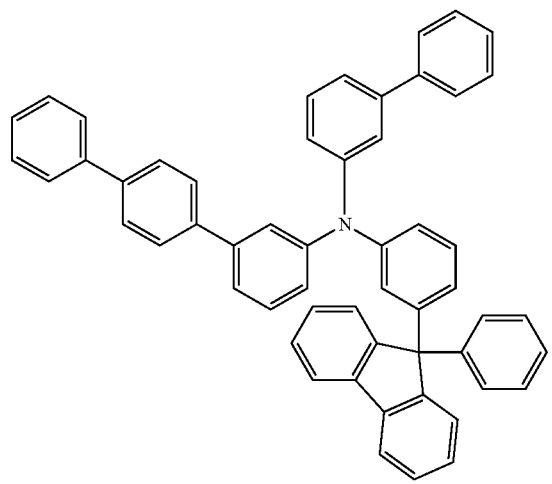
[32]
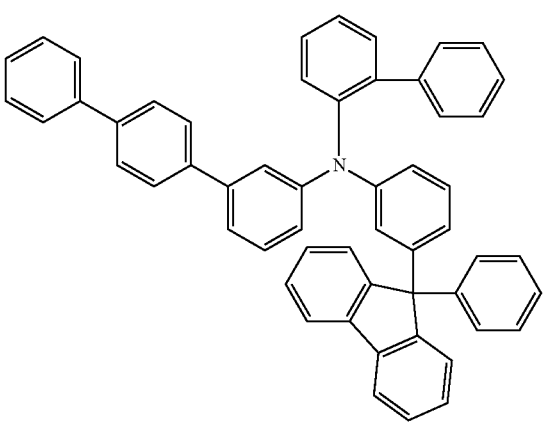
[33]
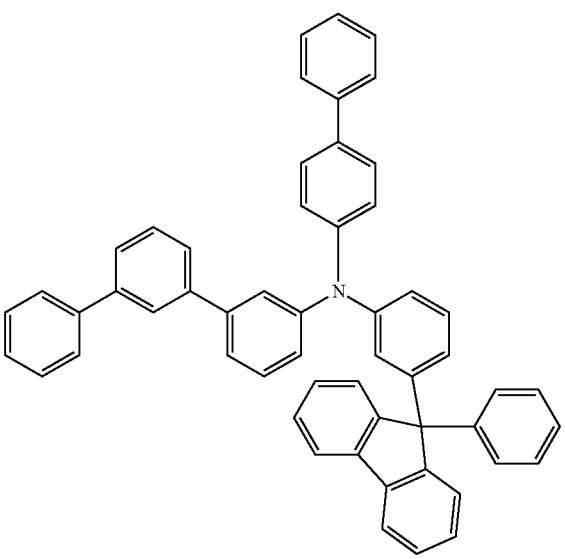
[34]
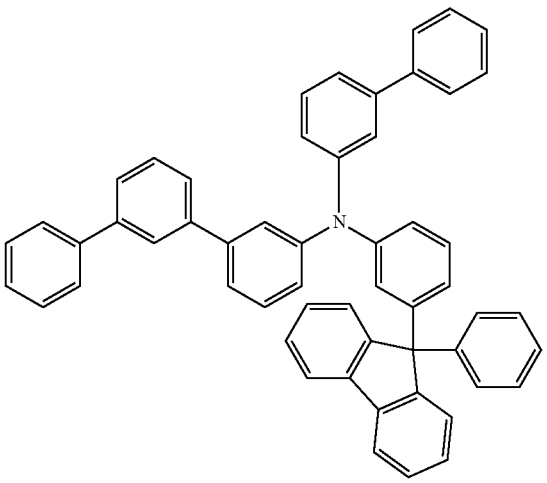

[35]
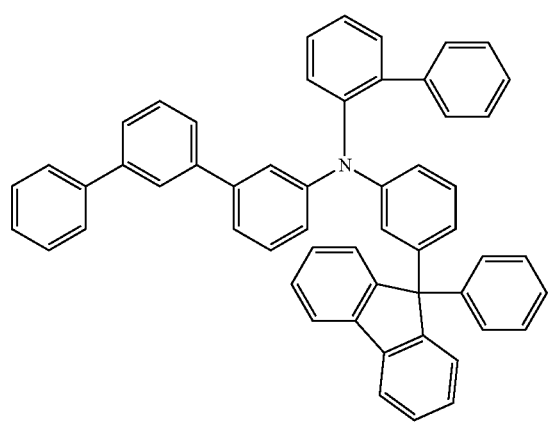
[38]
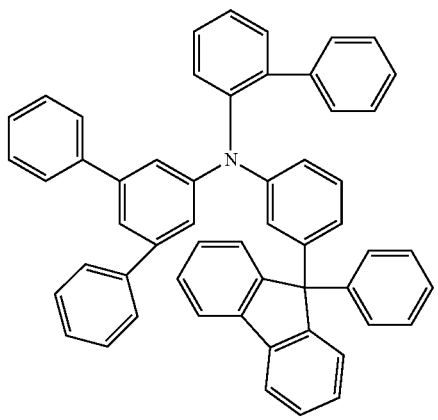
[36]
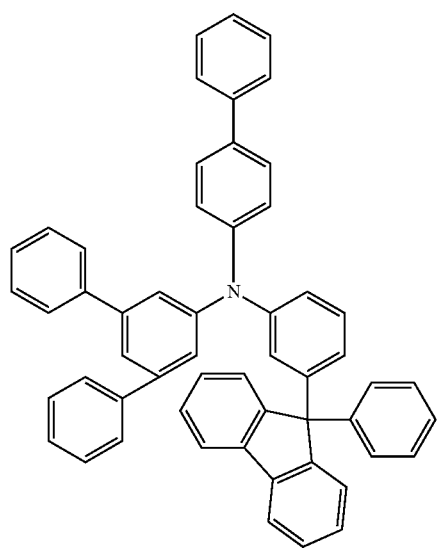
[37]
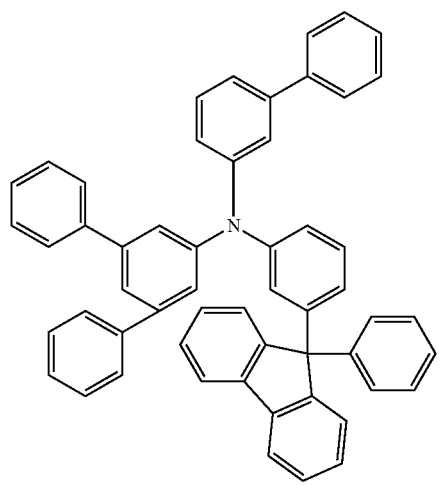
[39]
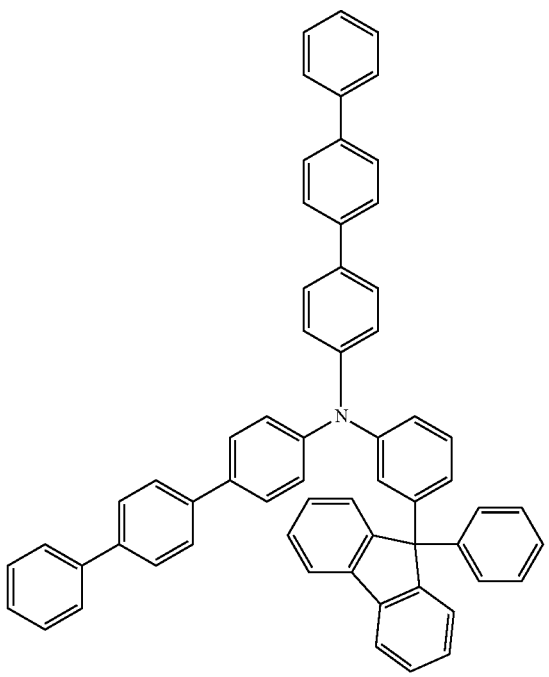

[40]
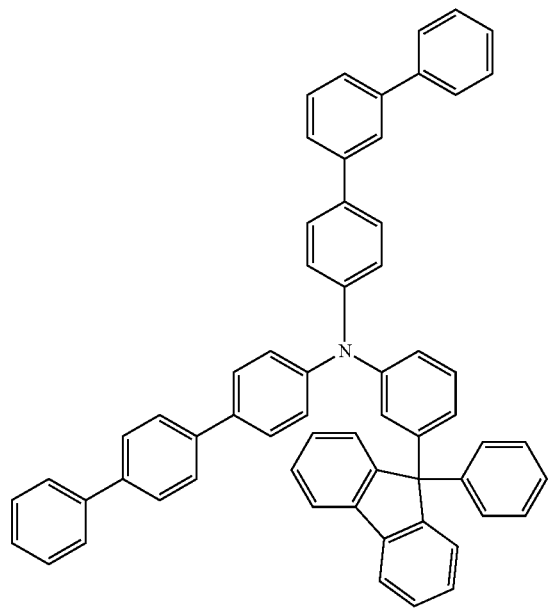
[42]
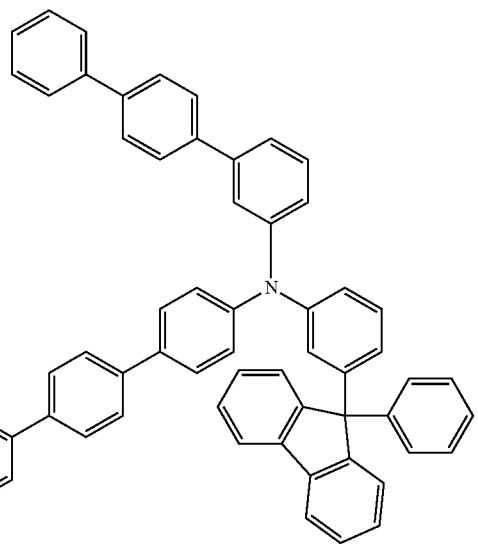
[41]
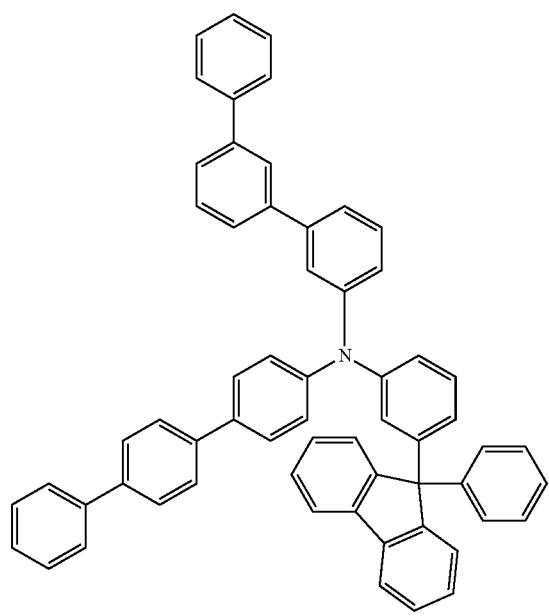
[43]
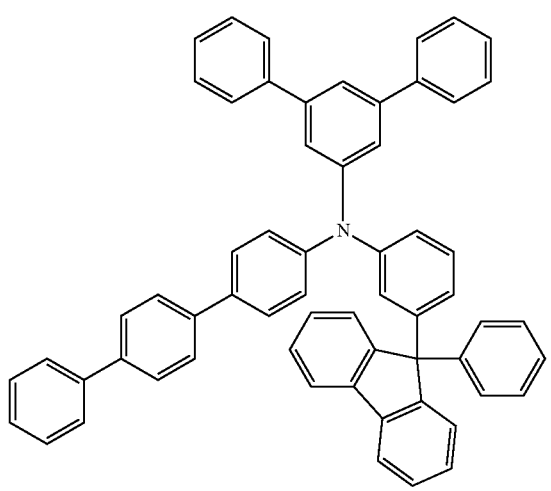

[44]
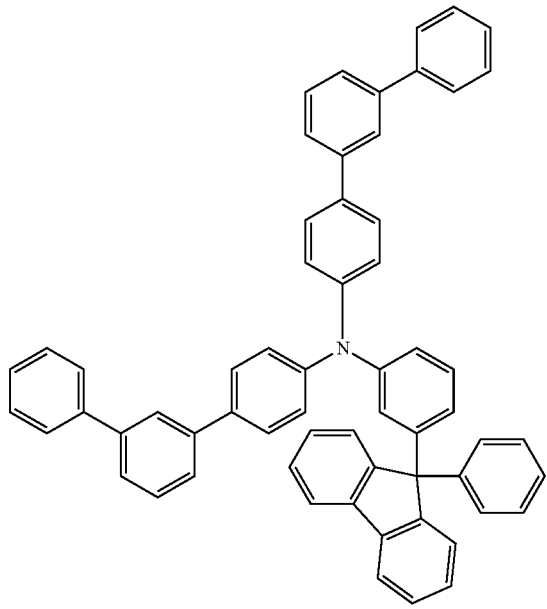

[45]
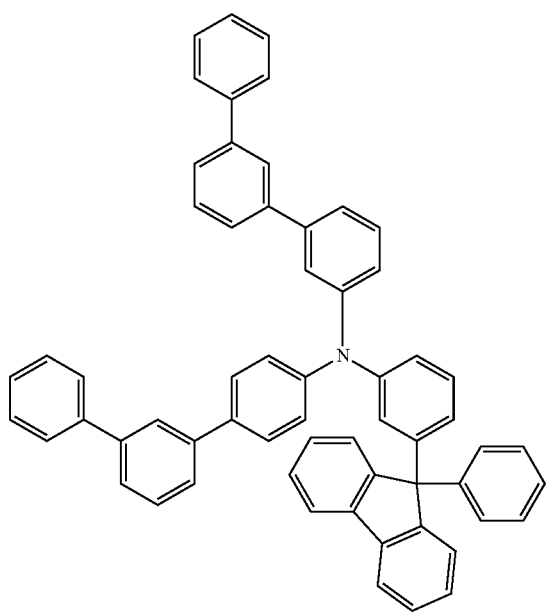

[46]
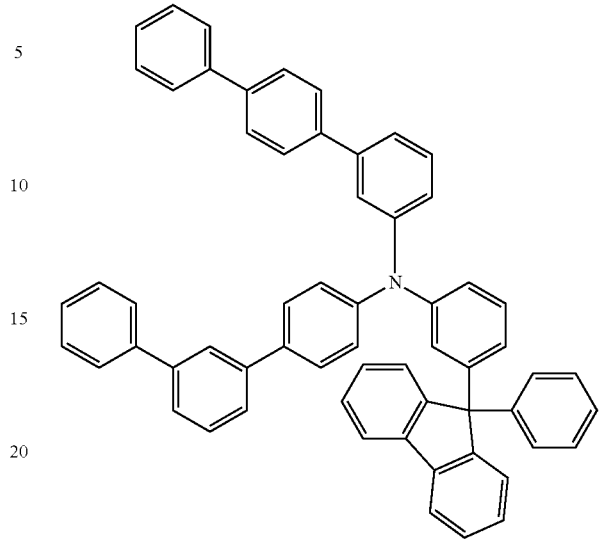

Hereinafter, an organic optoelectronic device including the aforementioned compound for an organic optoelectronic device is described.

The organic optoelectronic device may be a device that converts electrical energy into photoenergy and vice versa, e.g., an organic photoelectric device, an organic light emitting diode, an organic solar cell, or an organic photoconductor drum.

Herein, an organic light emitting diode as one example of an organic optoelectronic device is described referring to the drawing.

The FIGURE is a cross-sectional view showing an organic light emitting diode according to an embodiment.

Referring to the FIGURE, an organic light emitting diode 200 according to an embodiment may include an anode 120 and a cathode 110 facing each other and an organic layer 105 between the anode 120 and cathode 110.

The organic layer 105 may include the aforementioned compound for an organic optoelectronic device according to an embodiment.

The organic layer 105 may include, e.g., a light emitting layer 130, and a hole auxiliary layer 140 (between the anode 120 and the light emitting layer 130). In an implementation, the hole auxiliary layer 140 may include the aforementioned compound for an organic optoelectronic device.

In an implementation, the hole auxiliary layer 140 may include, e.g., a hole transport layer, and a hole transport auxiliary layer between the light emitting layer 130 and the hole transport layer. In an implementation, the hole transport auxiliary layer may include the aforementioned compound for an organic optoelectronic device.

The anode 120 may be a conductor having a large work function to facilitate hole injection, e.g., a metal, a metal oxide, or a conductive polymer. In an implementation, the anode 120 may be, e.g., a metal such as nickel, platinum, vanadium, chromium, copper, zinc, gold, or the like or an alloy thereof; a metal oxide such as zinc oxide, indium oxide, indium tin oxide (ITO), indium zinc oxide (IZO), or the like; a combination of a metal and an oxide such as ZnO and Al or $SnO_2$ and Sb; or a conductive polymer such as poly(3-methylthiophene), poly(3,4-(ethylene-1,2-dioxy)thiophene) (PEDOT), polypyrrole, and polyaniline.

The cathode 110 may be a conductor having a small work function to facilitate electron injection, and may be, e.g., a metal, a metal oxide, or a conductive polymer. In an implementation, the cathode 110 may be, e.g., a metal such as magnesium, calcium, sodium, potassium, titanium, indium, yttrium, lithium, gadolinium, aluminum, silver, tin, lead, cesium, barium, or the like, or an alloy thereof or a multilayer structure material such as LiF/Al, $LiO_2$/Al, LiF/Ca, LiF/Al, and $BaF_2$/Ca.

The light emitting layer 130 may include at least one host and a dopant.

The host may be a suitable host material, e.g., it may be a single host or a mixed host.

The dopant may be, e.g., a phosphorescent dopant. The dopant may be, e.g., a red, green or blue phosphorescent dopant.

Examples of the phosphorescent dopant may include organometallic compounds including Ir, Pt, Os, Ti, Zr, Hf, Eu, Tb, Tm, Fe, Co, Ni, Ru, Rh, Pd, or a combination thereof. In an implementation, the phosphorescent dopant may be, e.g., a compound represented by Chemical Formula Z.

LMX$^a$ [Chemical Formula Z]

In Chemical Formula Z, M may be, e.g., a metal, and L and X$^a$ may each independently be, e.g., ligands forming a complex compound with M.

The M may be, e.g., Ir, Pt, Os, Ti, Zr, Hf, Eu, Tb, Tm, Fe, Co, Ni, Ru, Rh, Pd, or a combination thereof, and L and X$^a$ may be, e.g., a bidentate ligand.

In an implementation, M may be, e.g., Ir or Pt.

In an implementation, the dopant may be a material mixed with the compound for an organic optoelectronic device in a small amount in the light emitting layer 130 to cause light emission, and may be generally a material such as a metal complex that emits light by multiple excitation into a triplet or more. The dopant may be, e.g., an inorganic, organic, or organic/inorganic compound, and one or more types thereof may be used.

In an implementation, the organic layer 105 may further include an electron transport layer, an electron injection layer, a hole injection layer, or the like.

The organic light emitting diode 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

(Preparation of Compound for Organic Optoelectronic Device)

Synthesis Example 1: Synthesis of Intermediate M-1

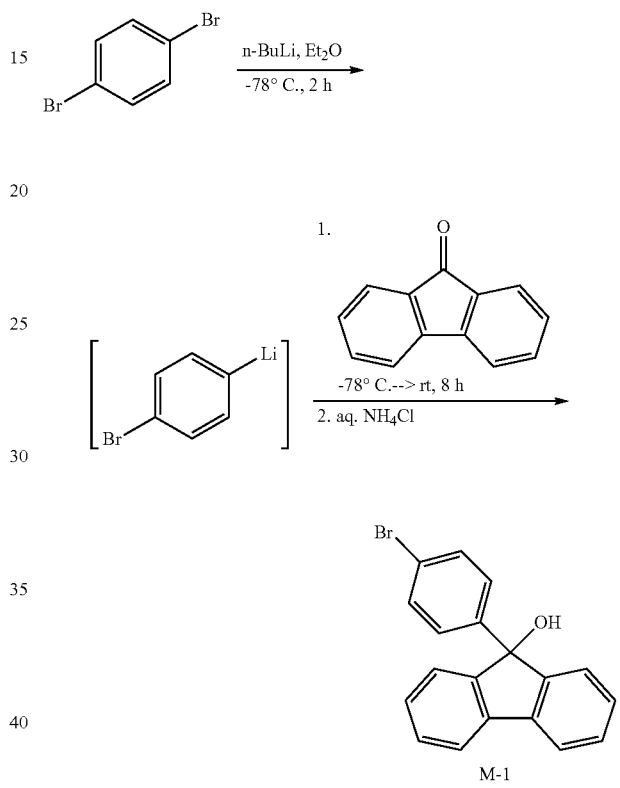

56.2 g (238.1 mmol) of 1,4-dibromobenzene was put in a round-bottomed flask heated and dried under a reduced pressure, and 500 ml of anhydrous diethyl ether was added thereto to dissolve it and then, cooled down to −78° C. and stirred under a nitrogen atmosphere. 100 ml (250 mmol) of a 2.5 M n-butyl lithium n-hexane solution was slowly added thereto and then, stirred at −78° C. under a nitrogen atmosphere for 2 hours. 41 g (226 mmol) of 9-fluorenone dissolved in 100 ml of anhydrous tetrahydrofuran was slowly added thereto and then, stirred at ambient temperature under a nitrogen atmosphere for 8 hours. The reaction solution was cooled down to 0° C., 250 ml of a 1.0 M ammonium chloride aqueous solution was added thereto, diethyl ether was used for extraction, an organic layer therefrom was dried with magnesium sulfate and filtered, and the filtered solution was concentrated under a reduced pressure. The residue was separated with a 10% ethyl acetate/n-hexane solution through silica gel column chromatography to obtain 70 g (Yield of 92%) of Intermediate M-1, a target compound.

LC-Mass (Theoretical value: 336.01 g/mol, Measured value: M+1=337.17 g/mol)

Synthesis Example 2: Synthesis of Intermediate M-2

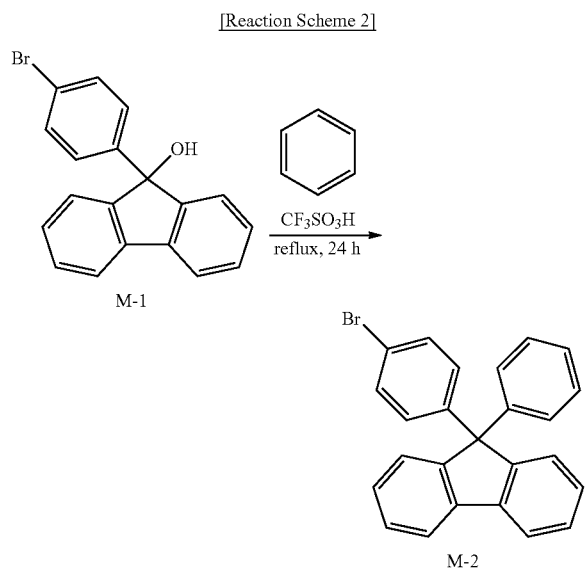

[Reaction Scheme 2]

M-1

M-2

In a round-bottomed flask, 67.4 g (200 mmol) of Intermediate M-1 was put, and 534 mL of benzene was added thereto to dissolve it. 30 g (200 mmol) of trifluoromethane sulfonic acid was slowly added thereto and then, refluxed and stirred under a nitrogen atmosphere for 24 hours. When a reaction was complete, 240 ml of a 1.0 M sodium bicarbonate aqueous solution was slowly added to the reaction solution, ethyl acetate and distilled water were used for extraction, and an organic layer therefrom was dried with magnesium sulfate and filtered, and a filtered solution therefrom was concentrated under a reduced pressure. A product therefrom was purified with n-hexane/dichloromethane (a volume ratio of 9:1) through silica gel column chromatography to obtain 27.8 g (Yield of 35%) of Intermediate M-2, a target compound.

LC-Mass (Theoretical value: 396.05 g/mol, Measured value: M+1=397.24 g/mol)

Synthesis Example 3: Synthesis of Intermediate M-3

[Reaction Scheme 3]

M-3

56.2 g (238.1 mmol) of 1,3-dibromobenzene was put in a round-bottomed flask heated and dried under a reduced pressure, and 500 ml of anhydrous diethyl ether was added thereto to dissolve it and then, cooled down to −78° C. and stirred under a nitrogen atmosphere. 100 ml (250 mmol) of a 2.5 M n-butyl lithium n-hexane solution was slowly added thereto and then, stirred at −78° C. under a nitrogen atmosphere for 2 hours. 41 g (226 mmol) of 9-fluorenone dissolved in 100 ml of anhydrous tetrahydrofuran was slowly added thereto and then, stirred at ambient temperature under a nitrogen atmosphere for 8 hours. The reaction solution was cooled down to 0° C., 250 ml of a 1.0 M ammonium chloride aqueous solution was added thereto, diethyl ether was used for an extraction, an organic layer therefrom was dried with magnesium sulfate and filtered, and the filtered solution was concentrated under a reduced pressure. The residue was separated with a 10% ethyl acetate/n-hexane solution through silica gel column chromatography to obtain 65 g (Yield of 85%) of Intermediate M-3, a target compound.

LC-Mass (Theoretical value: 336.01 g/mol, Measured value: M+1=337.21 g/mol)

Synthesis Example 4: Synthesis of Intermediate M-4

[Reaction Scheme 4]

M-3

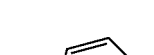

M-4

60 g (178 mmol) of Intermediate M-3 was put in a round-bottomed flask, and 476 mL of benzene was added thereto to dissolve it. 26.7 g (200 mmol) of trifluoromethane sulfonic acid was slowly added thereto and then, refluxed and stirred under a nitrogen atmosphere for 24 hours. When a reaction was complete, 214 ml of a 1.0 M sodium bicarbonate aqueous solution was slowly added thereto, ethyl acetate and distilled water were used for extraction, an organic layer magnesium sulfate dried with magnesium sulfate and filtered, and the filtered solution was concentrated under a reduced pressure. A product therefrom was purified with n-hexane/dichloromethane (a volume ratio of 9:1) through silica gel column chromatography obtain 30.4 g (Yield of 43%) of Intermediate M-4, a target compound.

LC-Mass (Theoretical value: 396.05 g/mol, Measured value: M+1=397.29 g/mol)

Synthesis Example 5: Synthesis of Intermediate M-5

[Reaction Scheme 5]

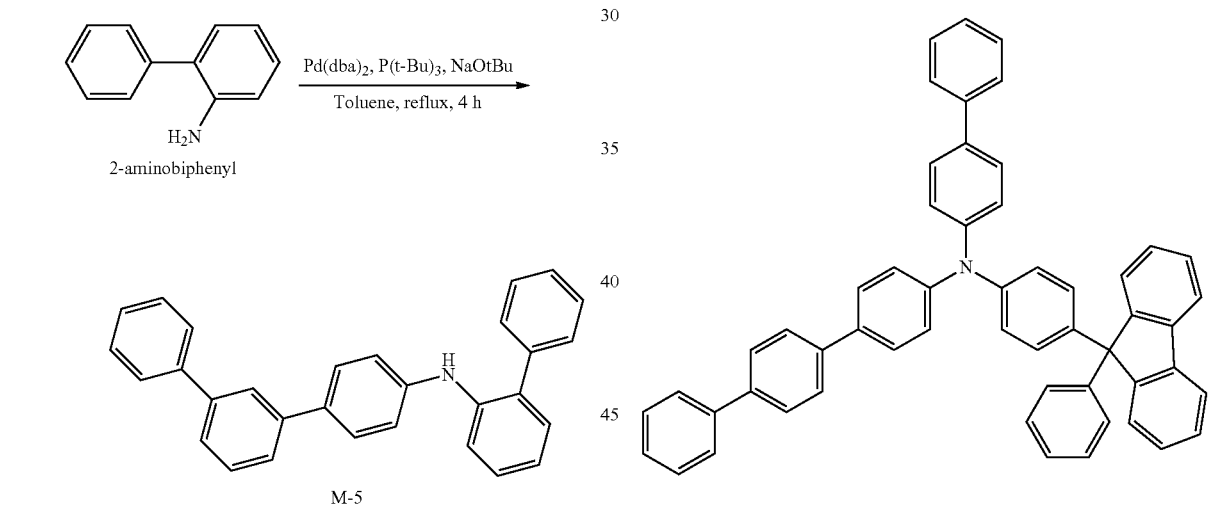

M-5

4.0 g (23.6 mmol) of 2-aminobiphenyl, 7.3 g (23.6 mmol) of 4-bromo-meta-terphenyl, and 3.4 g (35.4 mmol) of sodium t-butoxide were put in a round-bottomed flask, and 120 ml of toluene was added thereto to dissolve it. 0.14 g (0.24 mmol) of Pd(dba)₂ and 0.12 g (0.60 mmol) of tri-tert-butylphosphine were sequentially added thereto and then, refluxed and stirred under a nitrogen atmosphere for 4 hours. The reaction solution was extracted with toluene and distilled water, an organic layer therefrom was dried with magnesium sulfate and filtered, and the filtered solution was concentrated under a reduced pressure. A product was purified with n-hexane/dichloromethane (a volume ratio of 8:2) through silica gel column chromatography obtain 8.0 g (Yield of 85%) of Intermediate M-5, a target compound.

LC-Mass (Theoretical value: 397.18 g/mol, Measured value: M+1=398.54 g/mol)

Synthesis Example 6: Synthesis of Compound 1

[Reaction Scheme 6]

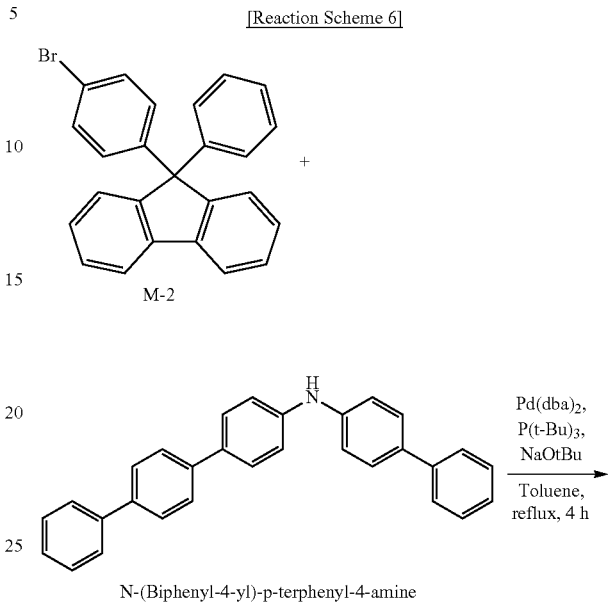

9.4 g (23.6 mmol) of N-(biphenyl-4-yl)-p-terphenyl-4-amine and 9.4 g (23.6 mmol) of Intermediate M-2, and 3.4 g (35.4 mmol) of sodium t-butoxide were put in a round-bottomed flask, and 240 ml of toluene was added thereto to dissolve it. 0.14 g (0.24 mmol) of Pd(dba)₂ and 0.12 g (0.60 mmol) of tri-tert-butylphosphine were sequentially added thereto and then, refluxed and stirred under a nitrogen atmosphere for 4 hours. When a reaction was complete, toluene and distilled water were used for extraction, an organic layer magnesium sulfate dried with magnesium sulfate and filtered, and the filtered solution was concentrated under a reduced pressure. A product therefrom was purified with n-hexane/dichloromethane (a volume ratio of 7:3) through silica gel column chromatography obtain 15.2 g (Yield of 90%) of Compound 1, a target compound.

LC-Mass (Theoretical value: 713.31 g/mol, Measured value: M+1=714.70 g/mol)

Synthesis Example 7: Synthesis of Compound 4

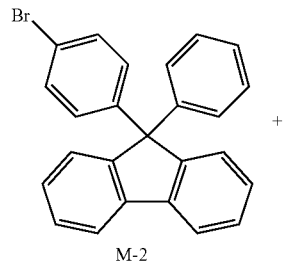

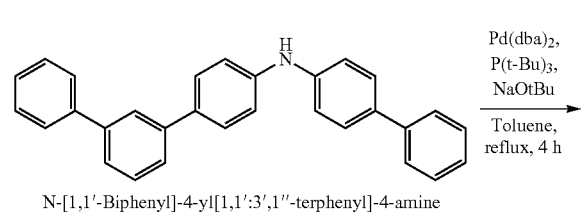

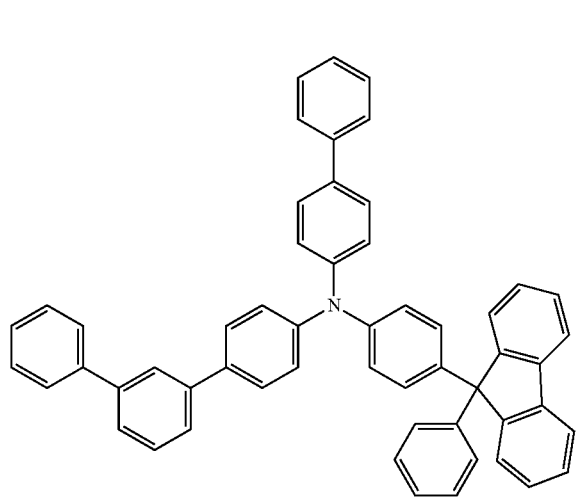

In a round-bottomed flask, 9.4 g (23.6 mmol) of N-[1,1'-biphenyl]-4-yl[1,1':3,1''-terphenyl]-4-amine, 9.4 g (23.6 mmol) of Intermediate M-2, and 3.4 g (35.4 mmol) of sodium t-butoxide were put, and 240 ml of toluene was added thereto to dissolve it. 0.14 g (0.24 mmol) of Pd(dba)$_2$ and 0.12 g (0.60 mmol) of tri-tert-butylphosphine were sequentially added thereto and then, refluxed and stirred under a nitrogen atmosphere for 4 hours. When a reaction was complete, toluene and distilled water were used for extraction, an organic layer therefrom was dried with magnesium sulfate and filtered, and the filtered solution was concentrated under a reduced pressure. A product was purified with n-hexane/dichloromethane (in a volume ratio of 7:3) through silica gel column chromatography to obtain 15.5 g (Yield of 92%) of Compound 4, a target compound.

LC-Mass (Theoretical value: 713.31 g/mol, Measured value: M+1=714.72 g/mol)

Synthesis Example 8: Synthesis of Compound 24

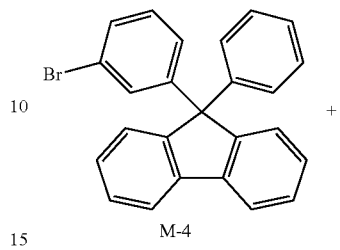

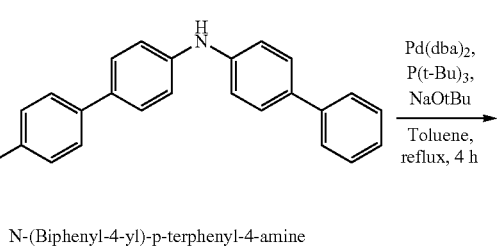

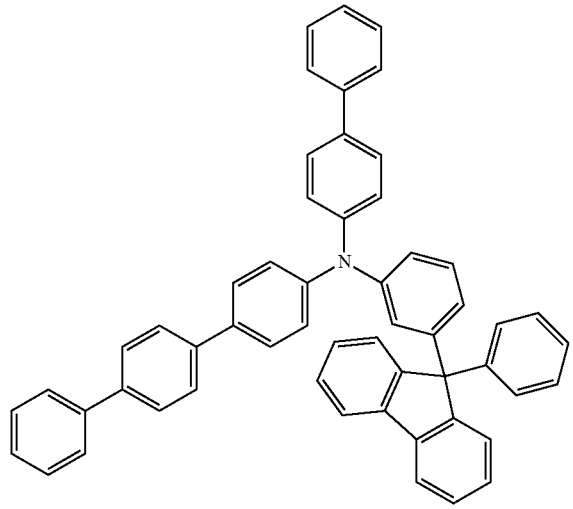

In a round-bottomed flask, 9.4 g (23.6 mmol) of N-(biphenyl-4-yl)-p-terphenyl-4-amine, 9.4 g (23.6 mmol) of Intermediate M-4, and 3.4 g (35.4 mmol) of sodium t-butoxide were put, and 240 ml of toluene was added thereto to dissolve it. 0.14 g (0.24 mmol) of Pd(dba)$_2$ and 0.12 g (0.60 mmol) of tri-tert-butylphosphine were sequentially added thereto and then, refluxed and stirred under a nitrogen atmosphere for 4 hours. When a reaction was complete, toluene and distilled water were used for extraction, an organic layer therefrom was dried with magnesium sulfate and filtered, and the filtered solution was concentrated under a reduced pressure. A product therefrom was purified with n-hexane/dichloromethane (a volume ratio of 7:3) through silica gel column chromatography to obtain 15.5 g (Yield of 92%) of Compound 24, a target compound.

LC-Mass (Theoretical value: 713.31 g/mol, Measured value: M+1=714.73 g/mol)

Synthesis Example 9: Synthesis of Compound 29

Comparative Synthesis Example 1: Synthesis of Compound Y-1

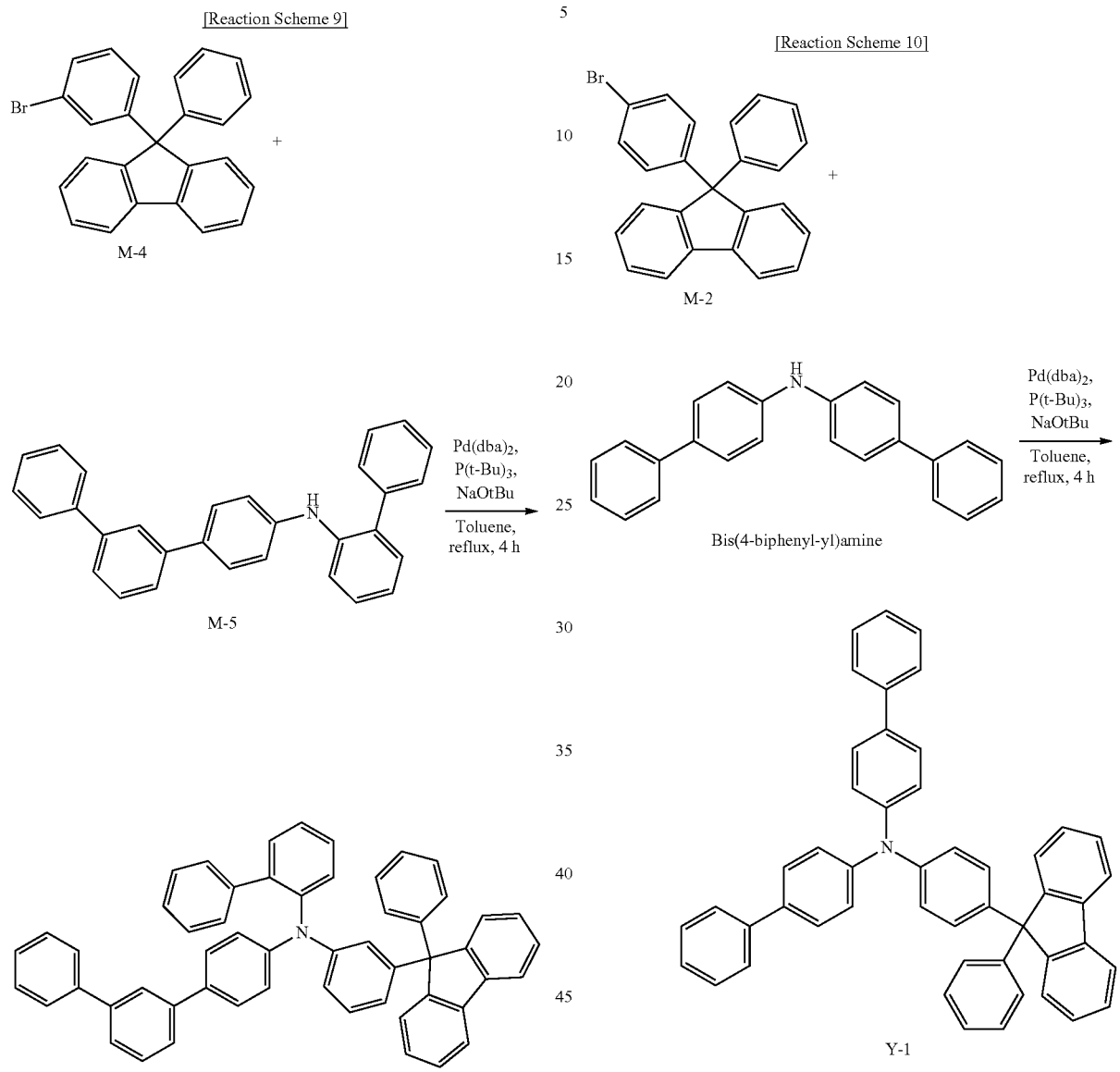

In a round-bottomed flask, 9.4 g (23.6 mmol) of Intermediate M-5, 9.4 g (23.6 mmol) of Intermediate M-4, and 3.4 g (35.4 mmol) of sodium t-butoxide were put and 240 ml of toluene was added thereto to dissolve them. 0.14 g (0.24 mmol) of Pd(dba)$_2$ and 0.12 g (0.60 mmol) of tri-tert-butylphosphine were sequentially added thereto and then, refluxed and stirred under a nitrogen atmosphere for 4 hours. When a reaction was complete, toluene and distilled water were used for extraction, an organic layer was dried with magnesium sulfate and filtered, and the filtered solution was concentrated under a reduced pressure. A product therefrom was purified with n-hexane/dichloromethane (a volume ratio of 7:3) through silica gel column chromatography to obtain 15.8 g (Yield of 94%) of Compound 29, a target compound.

LC-Mass (Theoretical value: 713.31 g/mol, Measured value: M+1=714.65 g/mol)

In a round-bottomed flask, 7.6 g (23.6 mmol) of bis(4-biphenyl-yl)amine, 9.4 g (23.6 mmol) of Intermediate M-2, and 3.4 g (35.4 mmol) of sodium t-butoxide were put, and 240 ml of toluene was added thereto to dissolve them. 0.14 g (0.24 mmol) of Pd(dba)$_2$ and 0.12 g (0.60 mmol) of tri-tert-butylphosphine were sequentially added thereto and then, refluxed and stirred under a nitrogen atmosphere for 4 hours. When a reaction was complete, toluene and distilled water were used for extraction, an organic layer therefrom was dried with magnesium sulfate and filtered, and the filtered solution was concentrated under a reduced pressure. A product therefrom was purified with n-hexane/dichloromethane (a volume ratio of 7:3) through silica gel column chromatography to obtain 13.5 g (Yield of 90%) of Compound Y-1.

LC-Mass (Theoretical value: 637.28 g/mol, Measured value: M+1=638.52 g/mol)

Comparative Synthesis Example 2: Synthesis of Compound Y-2

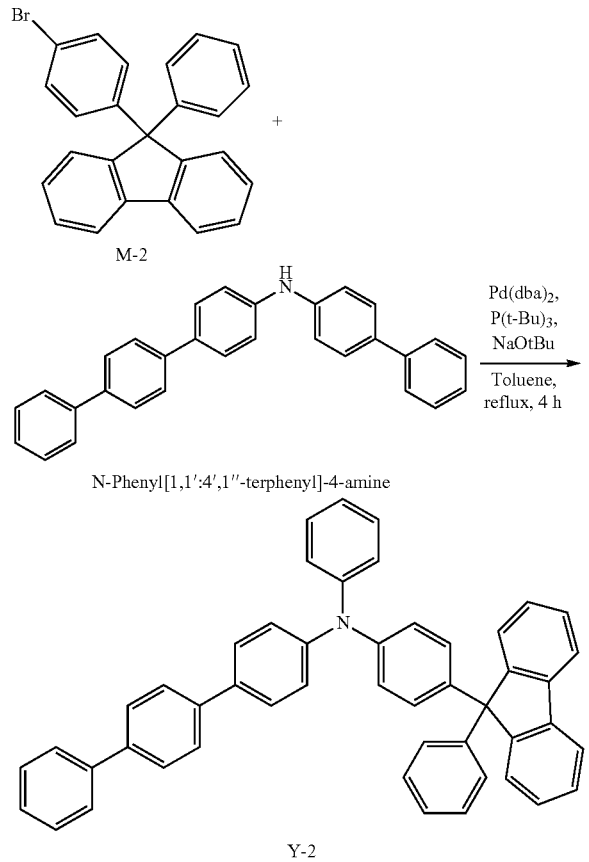

In a round-bottomed flask, 7.6 g (23.6 mmol) of N-phenyl [1,1':4',1''-terphenyl]-4-amine, 9.4 g (23.6 mmol) of Intermediate M-2, and 3.4 g (35.4 mmol) of sodium t-butoxide were dissolved in 240 ml of toluene. 0.14 g (0.24 mmol) of Pd(dba)$_2$ and 0.12 g (0.60 mmol) of tri-tert-butylphosphine were sequentially added thereto and then, refluxed and stirred under a nitrogen atmosphere for 4 hours. When a reaction was complete, toluene and distilled water were used for extraction, an organic layer therefrom was dried with magnesium sulfate and filtered, and the filtered solution was concentrated under a reduced pressure. A product therefrom was purified with n-hexane/dichloromethane (a volume ratio of 7:3) through silica gel column chromatography to obtain 13.4 g (Yield of 89%) of Compound Y-2.

LC-Mass (Theoretical value: 637.28 g/mol, Measured value: M+1=638.52 g/mol)

(Production of Organic Light Emitting Diode)
Production of Red Organic Light Emitting Diode Example 1

A glass substrate coated with ITO (Indium tin oxide) having a thickness of 1,500 Å was washed with distilled water. After washing with the distilled water, the glass substrate was ultrasonically washed with isopropyl alcohol, acetone, or methanol and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 700 Å-thick to form a hole transport layer. On the hole transport layer, Compound 1 of Synthesis Example 6 was vacuum-deposited to form a 700 Å-thick hole transport auxiliary layer. On the hole transport auxiliary layer, 400 Å-thick light emitting layer was formed by using Compound E as a host and doping 2 wt % of [Ir(piq)$_2$acac] as a dopant by a vacuum-deposition. Subsequently, on the light emitting layer, a 300 Å-thick electron transport layer was formed by simultaneously vacuum-depositing Compound D and Liq in a weight ratio of 1:1, and on the electron transport layer, Liq and Al were sequentially vacuum-deposited to be 15 Å-thick and 1,200 Å-thick, producing an organic light emitting diode.

The organic light emitting diode had a five-layered organic thin layer, and specifically the following structure.

ITO/Compound A (700 Å)/Compound B (50 Å)/Compound C (700 Å)/Compound 1 (700 Å)/EML [Compound E: [Ir(piq)$_2$acac] (2 wt %)] (400 Å)/Compound D: Liq (300 Å)/Liq (15 Å)/Al (1,200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN)

Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Compound E: 9-phenyl-9'-(4-phenylquinazolin-2-yl)-9H,9'H-3,3'-bicarbazole Examples 2 to 4

Organic light emitting diodes were produced according to the same method as Example 1 except that Compounds 4, 24, and 29 of Synthesis Examples 7 to 9 were respectively used instead of Compound 1 of Synthesis Example 6.

Comparative Examples 1 and 2

Organic light emitting diodes were produced according to the same method as Example 1 except that Compounds Y-1 and Y-2 of Comparative Synthesis Examples 1 and 2 were respectively used instead of Compound 1 of Synthesis Example 6.

Production of Green Organic Light Emitting Diode

Example 5

A glass substrate coated with ITO (Indium tin oxide) having a thickness of 1,500 Å was washed with distilled water. After washing with the distilled water, the glass substrate was ultrasonically washed with isopropyl alcohol, acetone, or methanol and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 700 Å-thick to form a hole transport layer. On the hole transport layer, Compound 1 of Synthesis Example 6 was vacuum-deposited to form a 700 Å-thick hole transport auxiliary layer. On the hole transport auxiliary layer, 400 Å-thick light emitting layer was formed by using Compound F as a host and doping 5 wt % of [Ir(ppy)$_3$] as a dopant by a vacuum-deposition. Subsequently, on the light emitting layer, a 300 Å-thick electron transport layer was formed by simultaneously vacuum-depositing Compound D and Liq in a weight ratio of 1:1, and on the electron transport layer, Liq and Al were sequentially vacuum-deposited to be 15 Å-thick and 1,200 Å-thick, producing an organic light emitting diode.

The organic light emitting diode had a five-layered organic thin layer, and specifically the following structure.

ITO/Compound A (700 Å)/Compound B (50 Å)/Compound C (700 Å)/Compound 1 (700 Å)/EML [Compound F: [Ir(ppy)$_3$] (5 wt %)] (400 Å)/Compound D: Liq (300 Å)/Liq (15 Å)/Al (1,200 Å).

Compound A: N4,N4'-diphenyl-N4,N4'-bis(9-phenyl-9H-carbazol-3-yl)biphenyl-4,4'-diamine
Compound B: 1,4,5,8,9,11-hexaazatriphenylene-hexacarbonitrile (HAT-CN)
Compound C: N-(biphenyl-4-yl)-9,9-dimethyl-N-(4-(9-phenyl-9H-carbazol-3-yl)phenyl)-9H-fluoren-2-amine
Compound D: 8-(4-(4,6-di(naphthalen-2-yl)-1,3,5-triazin-2-yl)phenyl)quinoline
Compound F: 9-(4,6-Diphenyl-1,3,5-triazin-2-yl)-9'-phenyl-3,3'-bicarbazole Examples 6 to 8

Organic light emitting diodes were manufacture according to the same method as Example 5 except that Compounds 4, 24, and 29 of Synthesis Examples 7 to 9 were respectively used instead of Compound 1 of Synthesis Example 6.

Comparative Examples 3 and 4

Organic light emitting diodes were manufacture according to the same method as Example 5 except that Compounds Y-1 and Y-2 of Comparative Synthesis Examples 1 and 2 were respectively used instead of Compound 1 of Synthesis Example 6.

Evaluation

Power efficiency of the organic light emitting diodes according to Examples 1 to 8 and Comparative Examples 1 to 4 was evaluated.

Specific measurement methods were as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Luminous efficiency (cd/A) at the same current density (10 mA/cm$^2$) were calculated by using the luminance and current density from the items (1) and (2).

(4) Measurement of Life-Span

The results were obtained by measuring a time when current efficiency (cd/A) was decreased down to 90%, while luminance (cd/m$^2$) was maintained to be 6,000 cd/m$^2$.

(5) Measurement of Driving Voltage

A driving voltage of each diode was measured using a current-voltage meter (Keithley 2400) at 15 mA/cm$^2$.

(6) Calculation of T90 Life-span Ratio (%) of Red Organic Light Emitting Diode

A T90 life-span ratio (%) was calculated by comparing T90(h) of Comparative Example 2 and Examples 1 to 4 with T90(h) of Comparative Example 1 using Compound Y-1 as a hole transport auxiliary layer.

T90 life-span ratio (%)={[T90(h) of Comparative Example 2 and Examples 1 to 4]/[T90(h) of Comparative Example 1]}×100

(7) Driving Voltage Ratio (%) of Red Organic Light Emitting Diode

Ratios of driving voltages (V) of Comparative Example 2 and Examples 1 to 4 vs. a driving voltage (V) of Comparative Example 1 using Compound Y-1 as a hole transport auxiliary layer were calculated.

Driving voltage ratio (%)={[Driving voltages (V) of Comparative Example 2 and Examples 1 to 4]/[Driving voltage (V) of Comparative Example 1]}×100

(8) Red Organic Light Emitting Diode Luminous Efficiency Ratio (%)

Ratios of luminous efficiency (cd/A) of Comparative Examples 2 and Examples 1 to 4 vs. luminous efficiency (cd/A) of Comparative Example 1 using Compound Y-1 as a hole transport auxiliary layer were calculated.

Luminous efficiency ratio (%)={[luminous efficiency (cd/A) of Comparative Example 2 and Examples 1 to 4]/[luminous efficiency (cd/A) of Comparative Example 1]}×100

(9) T90 Life-Span Ratio (%) of Green Organic Light Emitting Diode

Ratios of T90(h) of Comparative Example 4 and Examples 5 to 8 vs. T90(h) of Comparative Example 3 using Compound Y-1 as a hole transport auxiliary layer were calculated.

T90 life-span ratio (%)={[T90(h) of Comparative Example 4 and Examples 5 to 8]/[T90(h) of Comparative Example 3]}×100

(10) Driving Voltage Ratio (%) of Green Organic Light Emitting Diode

Ratios of driving voltages (V) of Comparative Example 4 and Examples 5 to 8 vs. a driving voltage (V) of Comparative Example 3 using Compound Y-1 as a hole transport auxiliary layer were calculated.

Driving voltage ratio (%)={[driving voltages (V) of Comparative Example 4 and Examples 5 to 8]/[driving voltage (V) of Comparative Example 3]}×100

(11) Luminous Efficiency Ratio (%) of Green Organic Light Emitting Diode

Ratios of luminous efficiency (cd/A) of Comparative Examples 4 and Examples 5 to 8 vs. luminous efficiency (cd/A) of Comparative Example 3 using Compound Y-1 as a hole transport auxiliary layer were calculated.

Luminous efficiency ratio (%)={[luminous efficiency (cd/A) of Comparative Example 4 and Examples 5 to 8]/[luminous efficiency (cd/A) of Comparative Example 3]}×100

TABLE 1

| Hole transport auxiliary layer | Color | Ratio of luminous efficiency (%) | Ratio of driving voltage (%) | Ratio of life-span T90 (%) |
|---|---|---|---|---|
| Example 1 | Compound 1 | red | 103 | 96 | 115 |
| Example 2 | Compound 4 | red | 106 | 98 | 120 |
| Example 3 | Compound 24 | red | 106 | 99 | 125 |
| Example 4 | Compound 29 | red | 105 | 98 | 118 |
| Comparative Example 1 | Y-1 | red | 100 | 100 | 100 |
| Comparative Example 2 | Y-2 | red | 99 | 100 | 103 |

Referring to Table 1, the red organic light emitting diodes according to Examples 1 to 4 exhibited improved driving voltage and efficiency and particularly, greater than or equal to 12% improved life-span compared with the red organic light emitting diodes according to Comparative Examples 1 and 2.

TABLE 2

| Hole transport auxiliary layer | Color | Ratio of luminous efficiency (%) | Ratio of driving voltage (%) | Ratio of life-span T90 (%) |
|---|---|---|---|---|
| Example 5 | Compound 1 | green | 104 | 96 | 115 |
| Example 6 | Compound 4 | green | 107 | 98 | 120 |
| Example 7 | Compound 24 | green | 105 | 98 | 120 |
| Example 8 | Compound 29 | green | 107 | 99 | 115 |
| Comparative Example 3 | Y-1 | green | 100 | 100 | 100 |
| Comparative Example 4 | Y-2 | green | 99 | 103 | 98 |

Referring to Table 2, the green organic light emitting diodes according to Examples 5 to 8 exhibited improved driving voltage and efficiency and particularly, greater than or equal to 15% improved life-span compared with the green organic light emitting diodes according to Comparative Examples 3 and 4.

By way of summation and review, an organic light emitting diode converts electrical energy into light, and the performance of organic light emitting diode may be influenced by the organic materials between electrodes.

One or more embodiments may provide a compound for an organic optoelectronic device capable of realizing an organic optoelectronic device having high efficiency and long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic device, the compound being represented by Chemical Formula 1C, Chemical Formula 1D, or Chemical Formula 1E:

[Chemical Formula 1C]

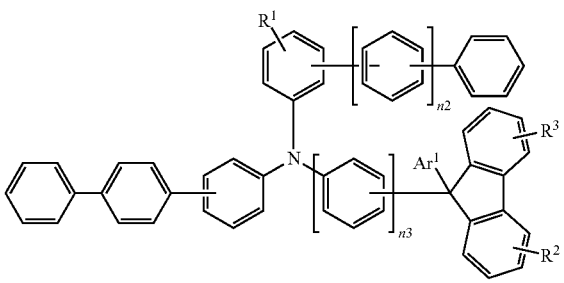

[Chemical Formula 1D]

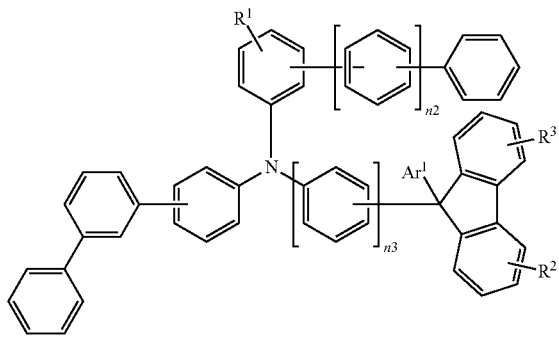

[Chemical Formula 1E]

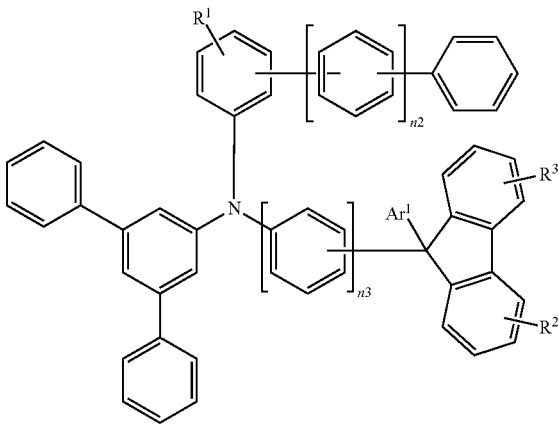

wherein, in Chemical Formula 1C, Chemical Formula 1D, and Chemical Formula 1E, $Ar^1$ is a substituted or unsubstituted C6 to C30 aryl group, $R^1$ to $R^3$ are independently hydrogen, deuterium, a cyano group, a halogen, a substituted or unsubstituted C1 to C10 alkyl group, or a phenyl group, n2 is an integer of 0 to 2, and n3 is 1 or 2.

2. The compound as claimed in claim 1, wherein:

the compound is represented by Chemical Formula 1C or Chemical Formula 1D,

Chemical Formula 1C is represented by Chemical Formula 1C-1,

Chemical Formula 1D is represented by Chemical Formula 1D-1,

[Chemical Formula 1C-1]

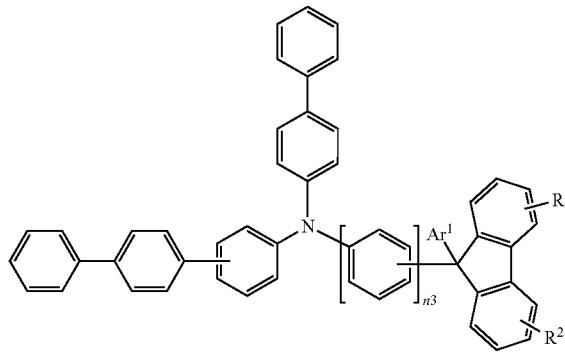

[Chemical Formula 1D-1]

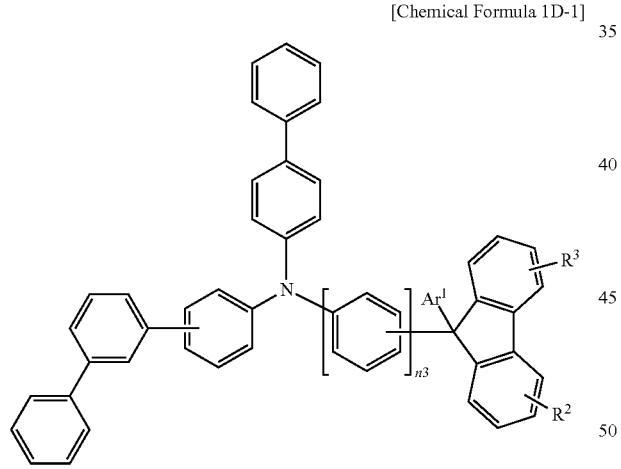

in Chemical Formula 1C-1 and Chemical Formula 1D-1, $Ar^1$ is a substituted or unsubstituted C6 to C20 aryl group, $R^2$ and $R^3$ are independently hydrogen, deuterium, a cyano group, a halogen, a substituted or unsubstituted C1 to C10 alkyl group, or a phenyl group, and n3 is 1 or 2.

3. The compound as claimed in claim 1, wherein $Ar^1$ is a phenyl group or a biphenyl group.

4. The compound as claimed in claim 1, wherein the compound represented by Chemical Formula 1 is a compound of Group 1:

[Group 1]

[1]

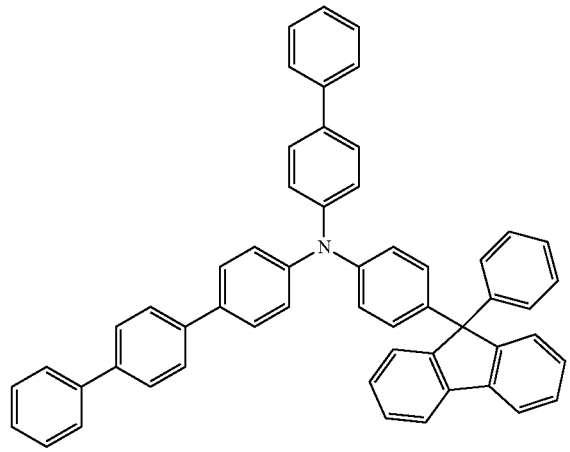

[2]

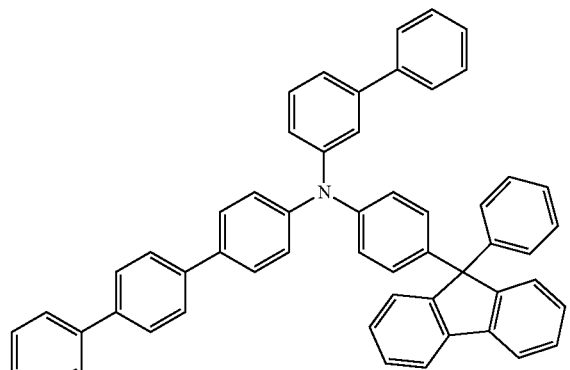

[3]

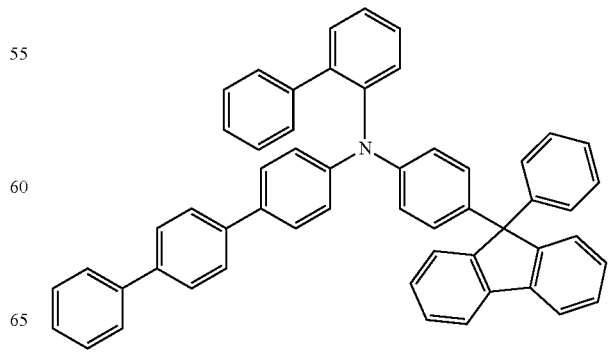

[4]
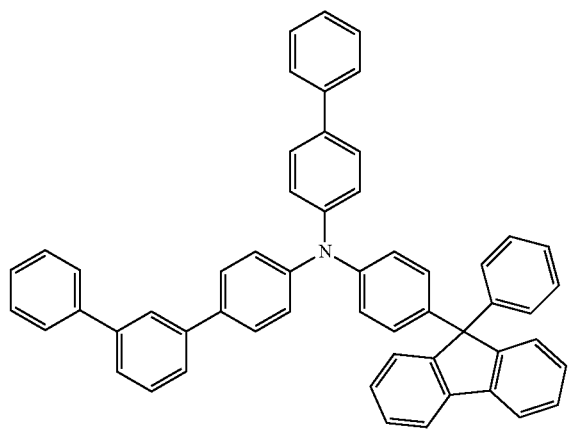
[5]
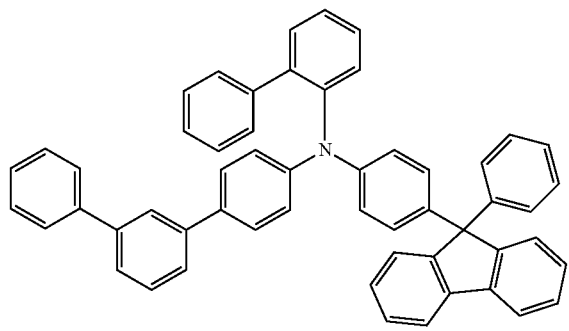
[6]
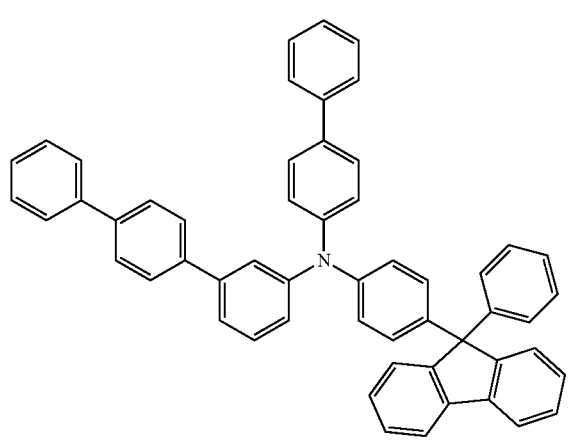
[7]
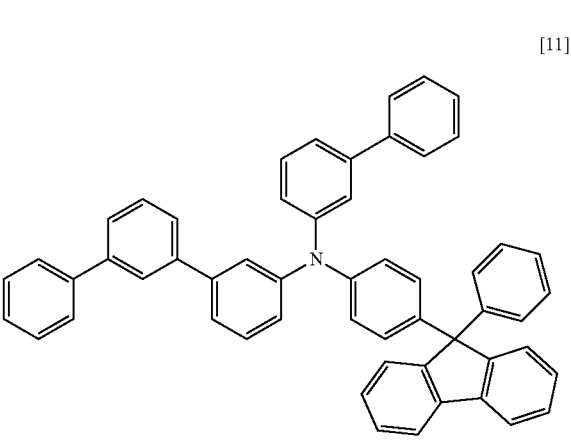
[8]
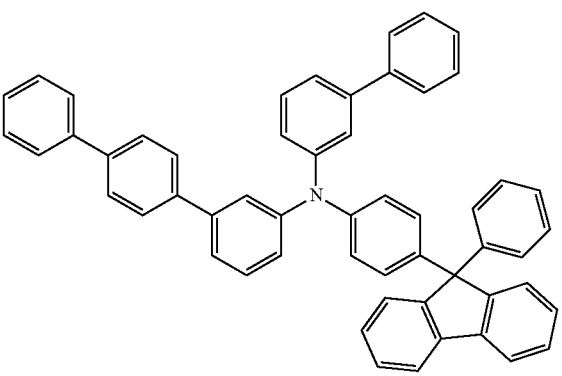
[9]
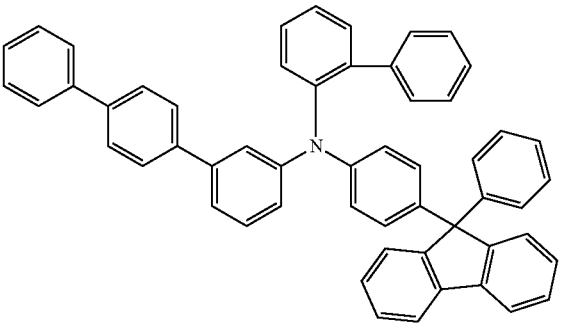
[10]
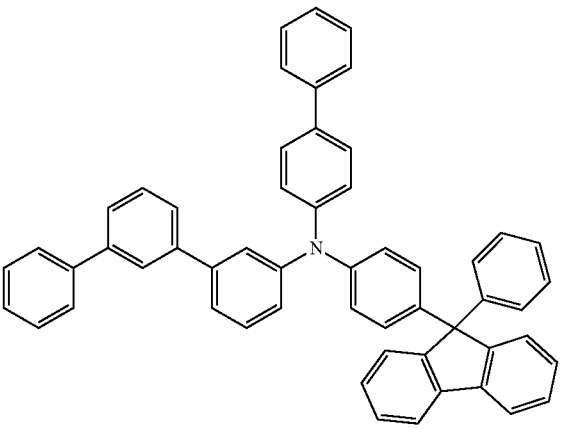
[11]

[12]
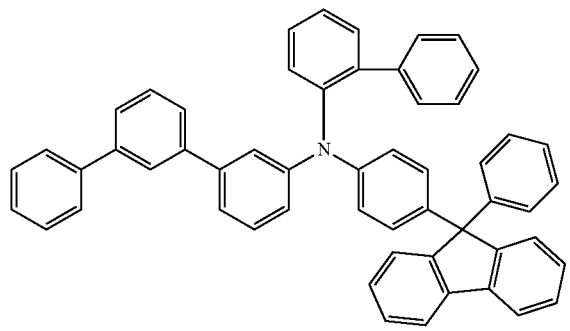
[13]
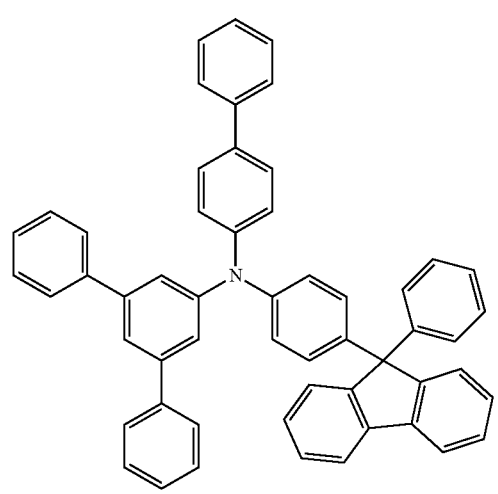
[14]
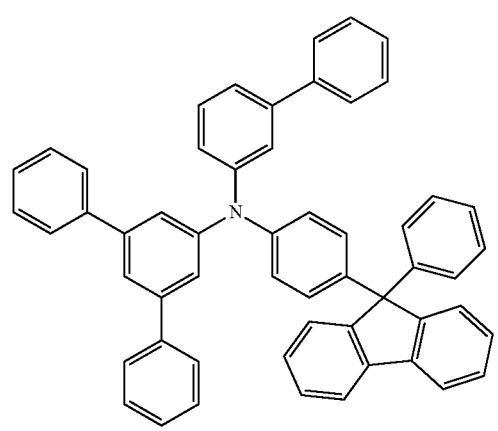
[15]
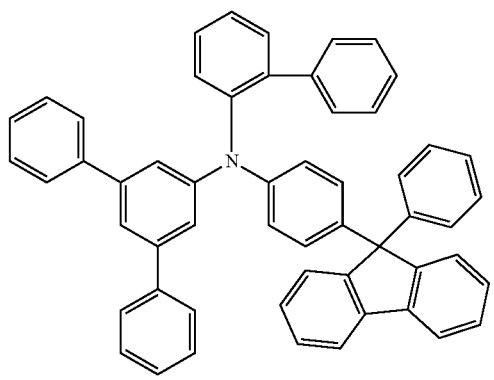
[16]
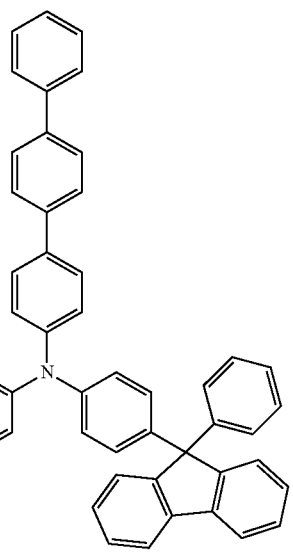
[17]
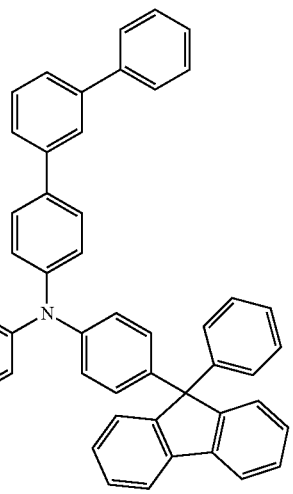

-continued
[18]
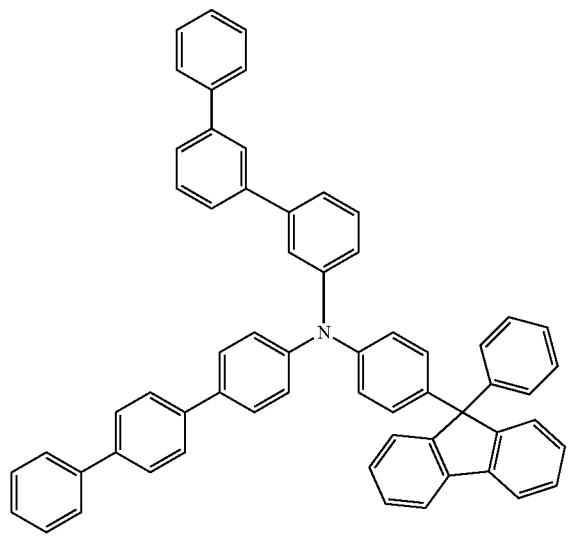
[19]
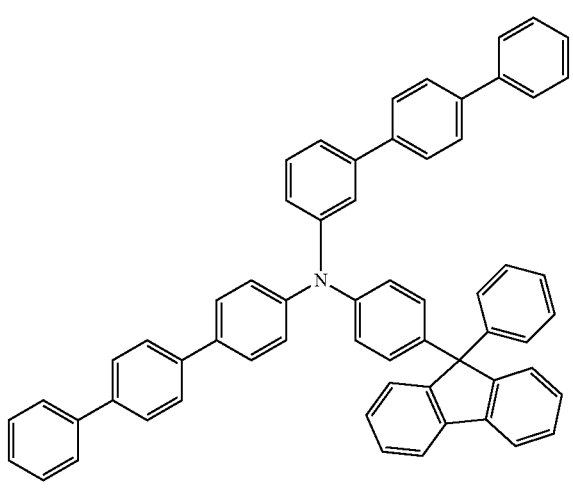
[20]
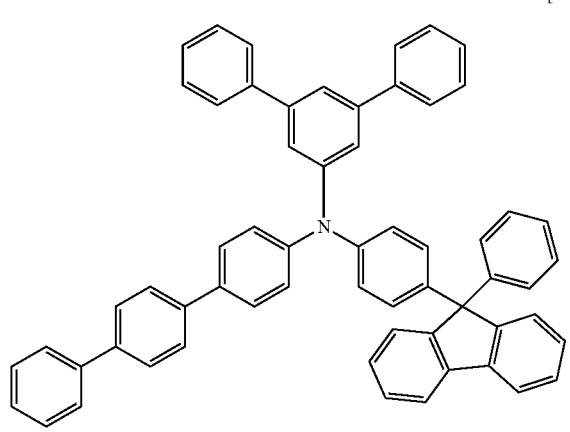
-continued
[21]
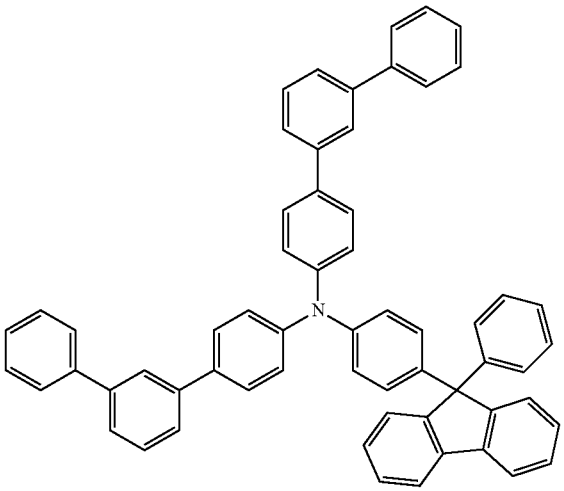
[22]
[23]
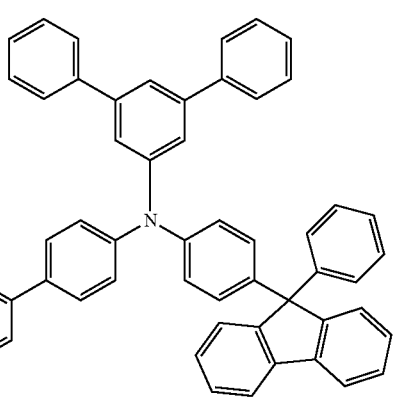

[24]
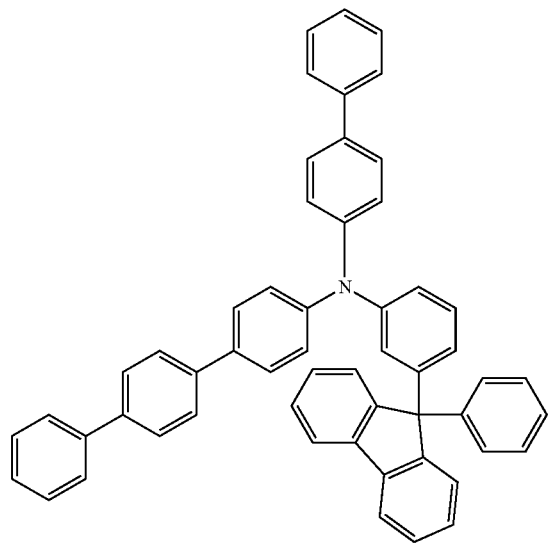
[25]
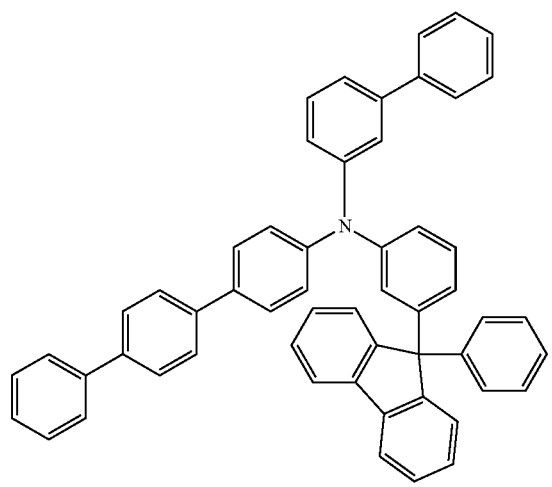
[26]
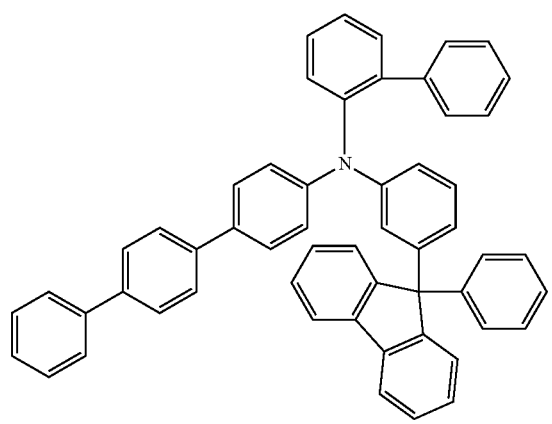
[27]
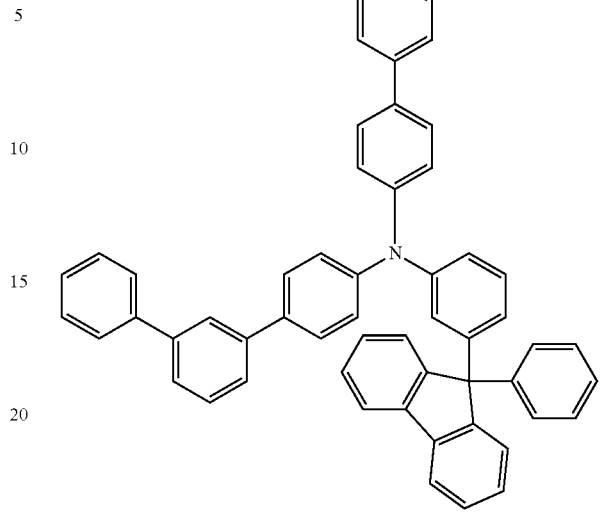
[28]
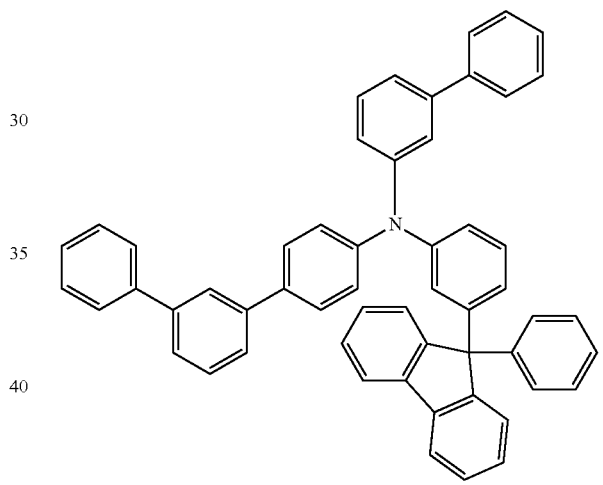
[29]
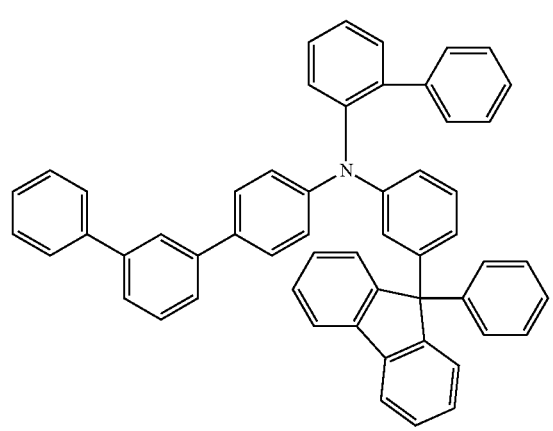

[30]
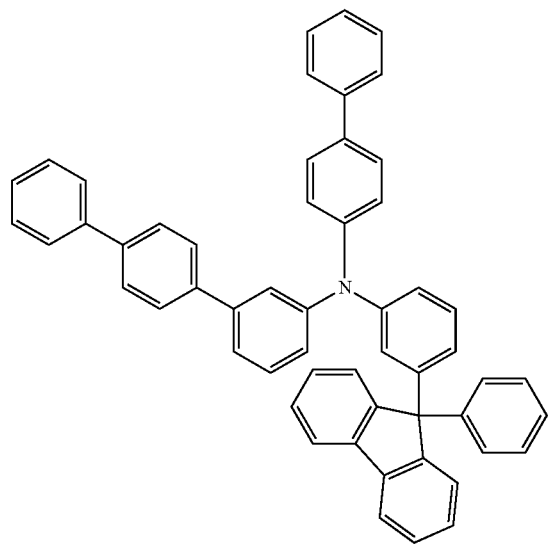
[31]
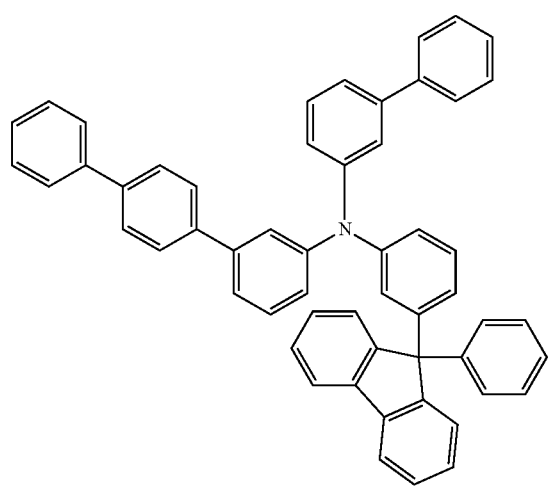
[32]
[33]
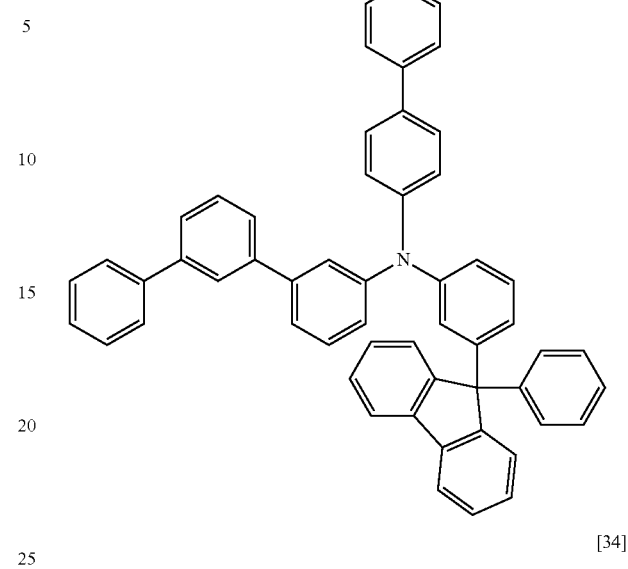
[34]
[35]
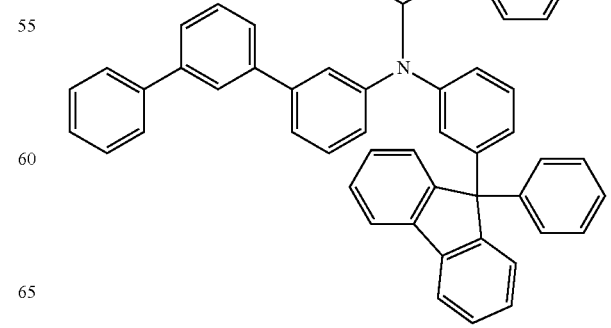

[36] 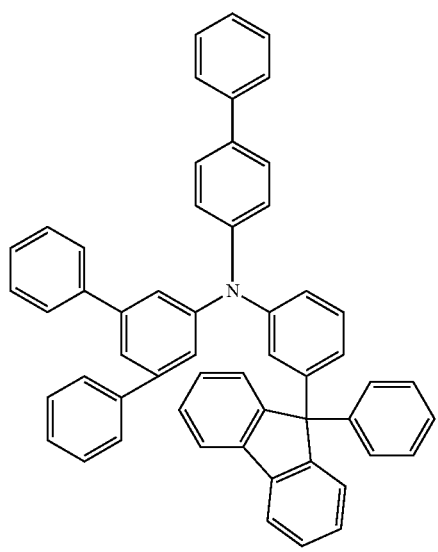
[37] 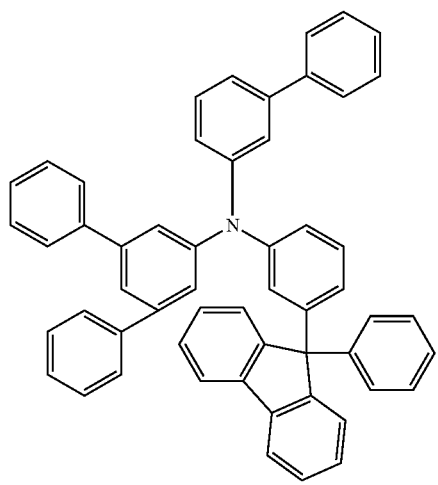
[38] 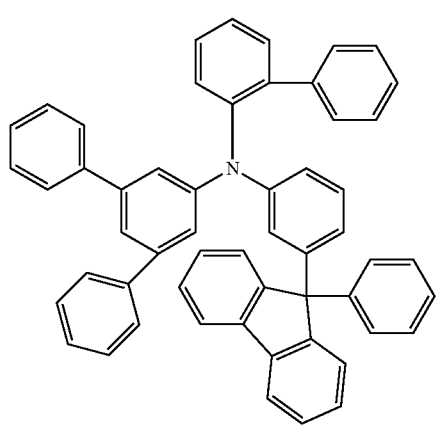
[39] 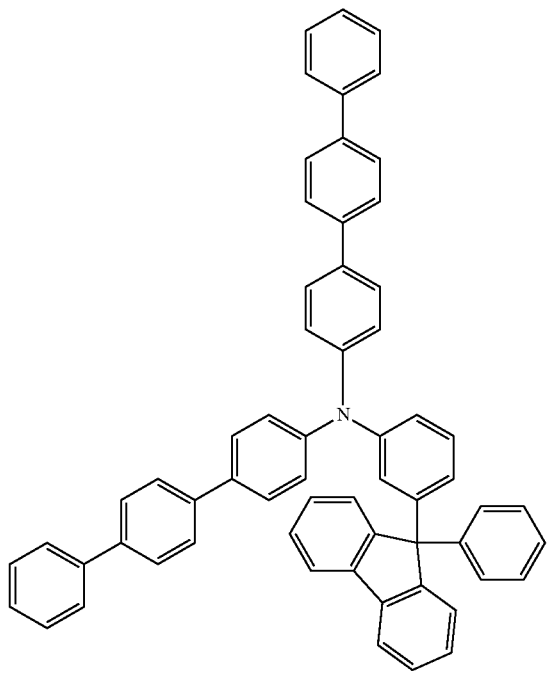
[40] 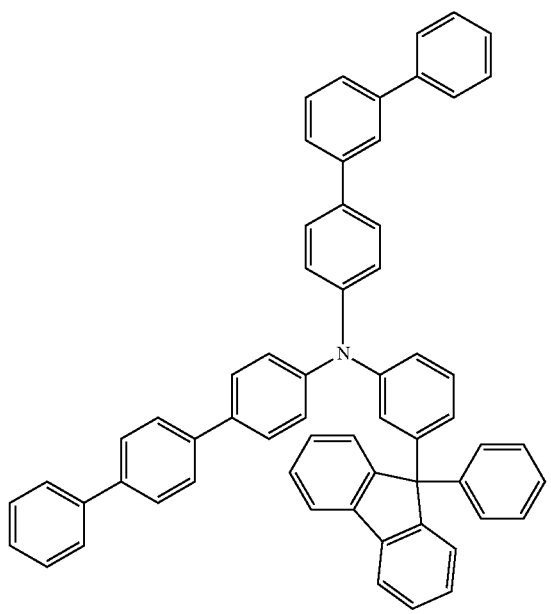

[41]
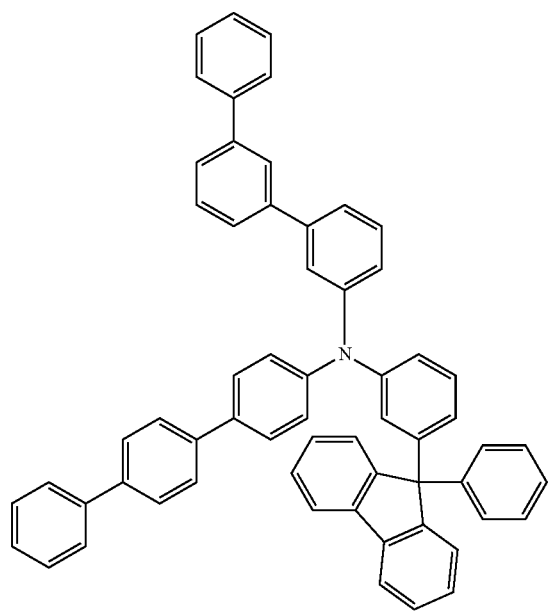
[42]
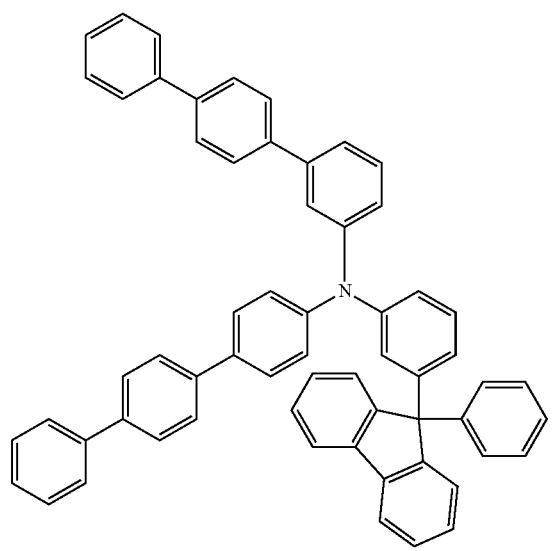
[43]
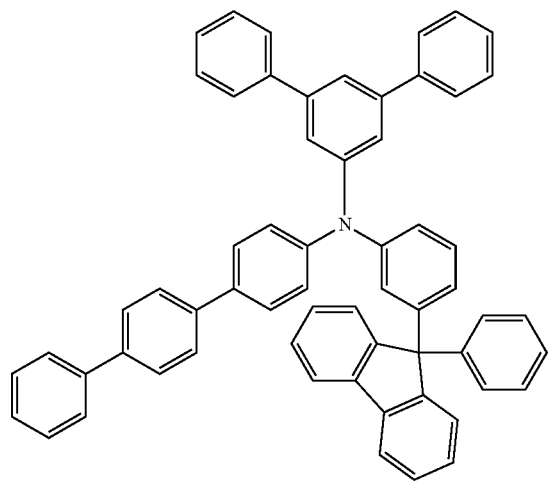
[44]
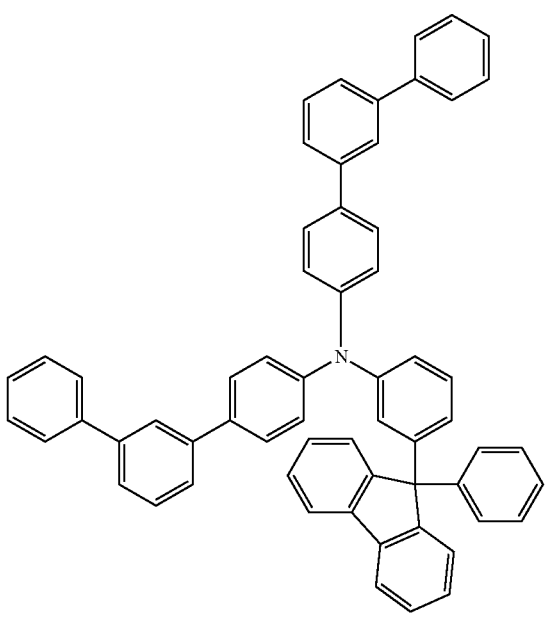
[45]
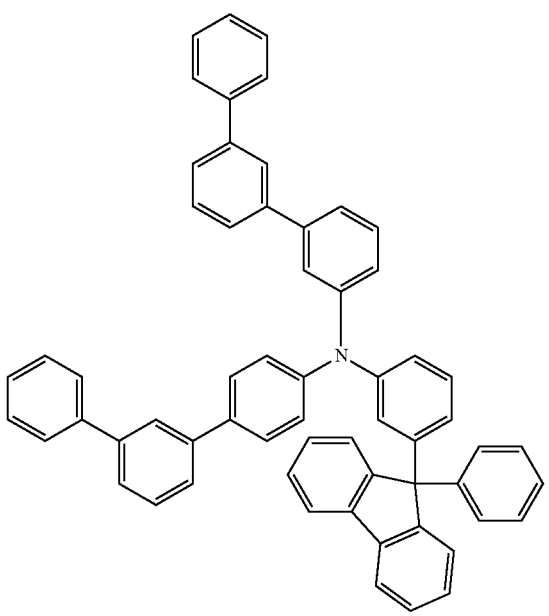

-continued

[46]

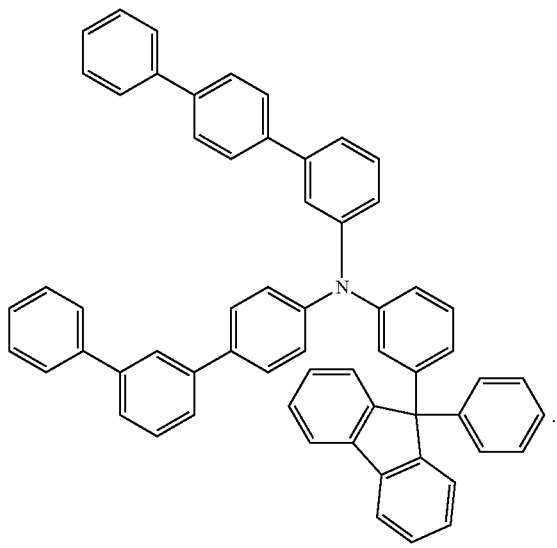

5. An organic optoelectronic device, comprising:
an anode and a cathode facing each other; and
at least one organic layer between the anode and the cathode,
wherein the at least one organic layer comprises the compound for an organic optoelectronic device as claimed in claim 1.

6. The organic optoelectronic device as claimed in claim 5, wherein:
the at least one organic layer comprises:
a light emitting layer, and
a hole auxiliary layer between the anode and the light emitting layer, and
the hole auxiliary layer comprises the compound for an organic optoelectronic device.

7. The organic optoelectronic device as claimed in claim 6, wherein:
the hole auxiliary layer comprises:
a hole transport layer, and
a hole transport auxiliary layer between the light emitting layer and the hole transport layer, and
the hole transport auxiliary layer comprises the compound for an organic optoelectronic device.

8. A display device comprising the organic optoelectronic device as claimed in claim 5.

* * * * *